(12) United States Patent
Niewiarowski et al.

(10) Patent No.: US 6,818,617 B1
(45) Date of Patent: Nov. 16, 2004

(54) EC-3, AN INHIBITOR OF α4β1 AND α4β7 INTEGRINS

(75) Inventors: Stefan Niewiarowski, Narbeth, PA (US); Cezary Marcinkiewicz, Philadelphia, PA (US)

(73) Assignee: Temple University- Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/485,323

(22) PCT Filed: Aug. 13, 1998

(86) PCT No.: PCT/US98/16719

§ 371 (c)(1),
(2), (4) Date: Feb. 7, 2000

(87) PCT Pub. No.: WO99/13898

PCT Pub. Date: Mar. 25, 1999

Related U.S. Application Data

(60) Provisional application No. 60/055,825, filed on Aug. 15, 1997, and provisional application No. 60/055,957, filed on Aug. 18, 1997.

(51) Int. Cl.[7] .................. A61K 38/16; C07K 14/46

(52) U.S. Cl. .................. 514/12; 514/13; 514/14; 514/15; 514/16; 514/17; 514/18; 530/324; 530/325; 530/326; 530/327; 530/328; 530/329; 530/330; 530/331; 530/344; 530/412; 530/415; 530/856

(58) Field of Search .................. 514/12, 13, 14, 514/15, 16, 17, 18; 530/324, 325, 326, 327, 328, 329, 330, 331, 344, 412, 415, 856; 424/183.1, 173.1, 184.1; 435/7.1, 7.8

(56) References Cited

U.S. PATENT DOCUMENTS

| | | | |
|---|---|---|---|
| 5,318,899 A | 6/1994 | Scarborough et al. | ..... 435/69.6 |
| 5,510,332 A | 4/1996 | Kogan et al. | ..... 514/14 |

FOREIGN PATENT DOCUMENTS

WO    WO 96/00581    1/1996

OTHER PUBLICATIONS

Vanderslice et al. 1997. A Cyclic hexapeptide is a potent antagonist of alpha4 integrins. J. Immunology 158:1710–1718.*

*The Merck Index*, Eighth Edition,. Edited by P. Stecher et al., Rahway, NJ, Merck & Co., Inc., 1968, p. 500.

Siigur et al., cDNA Cloning and Deduced Amino Acid Sequence of Fibrinolytic Enzyme (Lebetase) from Vipera Lebetina Snake Venom. *Biochemical and Biophysical Research Communications*, 224(1): 229–336 (1996).

Marchinkiewicz et al., "EC–3, A Novel MLD–Dependent Distintegrin From E. Carinatus Is A Potent Antagonist of α4 Integrins", *Molecular Biology of the Cell Supp.*, vol. 8, Abstract 1682 (Nov. 1997).

Marcinkiewicz et al., "Isolation and characterization of two novel dimeric disintegrins: EC–3 and EMF–10 inhibiting interaction of lymphoid cells with VCAM–1", *Blood*, 90(10: 59b Suppl. 1, Abstract 2966 (Nov. 15, 1997).

* cited by examiner

*Primary Examiner*—Robert A. Wax
(74) *Attorney, Agent, or Firm*—Drinker Biddle & Reath LLP

(57) ABSTRACT

This invention relates to the identification, purification, and characterization of a novel heterodimeric disintegrin, EC-3, from *Echis carinatus* viper venom. EC-3 inhibits α4 integrins in an RGD-independent manner. The invention further relates to methods of using EC-3, or a biologically active fragment or derivative thereof, to inhibit the interaction between cells expressing α4 integrins and cellular ligands.

24 Claims, 11 Drawing Sheets

Eristostatin           QEEPCATGPCCRRCKFKRAGKVCRVA  RGD  WNDDYCTGKSCDCPRNPWNG
Echistatin             ECESGPCCRNCKFLKEGTICKRA     RGD  DMDDYCNGKTCDCPRNPHKGPAT
Flavoridin   GEECDCGSPSNPCCDAATCKLRPGAQCADGLCCDQCRFKKKTGICRIA  RGD  FPDDRCTGLSNDCPRWNDL
Kistrin      GKECDCSSPENPCCDATCKLRPGAQCGEGLCCEQCKFSRAGKICRIP    RGD  MPDDRCTGQSADCPRYH
EC3A                   NSVHPCCDPVKCEPREGEHCISGPCCRNCKFLRAGTVCKRA    VGD  DVDDYCSGITPDCPRNRYKGKED
EC3B                   NSVHPCCDPVKCEPREGEHCISGPCCRNCKFLNAGTICKRA    MLD  GLNDYCTGKSSDCPRNRYKGKED
Le3 (disintegrin domain)  ...NSGNPCCDPVTCQPRRGEHCVSGKCCRNCKFLRAGTVCKRA  VGD  DMDDYCTGISSDCPRNPYKD

FIG. 5

SEQUENCE LISTING

<160> NUMBER OF SEQ ID NOS: 20

<210> SEQ ID NO 1
<211> LENGTH: 24
<212> TYPE: PRT
<213> ORGANISM: Echis carinatus
<220> FEATURE:
<221> NAME/KEY: VARIANT
<222> LOCATION: (11)
<223> OTHER INFORMATION: K or T
<221> NAME/KEY: UNSURE
<222> LOCATION: (6)
<223> OTHER INFORMATION: preliminary amino acid sequence
<221> NAME/KEY: UNSURE
<222> LOCATION: (7)
<223> OTHER INFORMATION: preliminary amino acid sequence
<221> NAME/KEY: UNSURE
<222> LOCATION: (12)
<223> OTHER INFORMATION: preliminary amino acid sequence
<221> NAME/KEY: UNSURE
<222> LOCATION: (20)
<223> OTHER INFORMATION: preliminary amino acid sequence

<400> SEQUENCE: 1

Asn Ser Val His Pro Xaa Xaa Asp Pro Val Xaa Xaa Glu Pro Arg Glu
 1               5                  10                  15

Gly Glu His Xaa Ile Ser Gly Pro
            20

<210> SEQ ID NO 2
<211> LENGTH: 67
<212> TYPE: PRT
<213> ORGANISM: Echis carinatus

```
<400> SEQUENCE: 2

Asn Ser Val His Pro Cys Cys Asp Pro Val Lys Cys Glu Pro Arg Glu
 1               5                  10                  15

Gly Glu His Cys Ile Ser Gly Pro Cys Cys Arg Asn Cys Tyr Phe Leu
            20                  25                  30

Arg Ala Gly Thr Val Cys Lys Arg Ala Val Gly Asp Asp Val Asp Asp
        35                  40                  45

Tyr Cys Ser Gly Ile Thr Pro Asp Cys Pro Arg Asn Arg Tyr Lys Gly
 50                  55                  60

Lys Glu Asp
 65

<210> SEQ ID NO 3
<211> LENGTH: 67
<212> TYPE: PRT
<213> ORGANISM: Echis carinatus

<400> SEQUENCE: 3

Asn Ser Val His Pro Cys Cys Asp Pro Val Lys Cys Glu Pro Arg Glu
 1               5                  10                  15

Gly Glu His Cys Ile Ser Gly Pro Cys Cys Arg Asn Cys Lys Phe Leu
            20                  25                  30

Asn Ala Gly Thr Ile Cys Lys Arg Ala Met Leu Asp Gly Leu Asn Asp
        35                  40                  45

Tyr Cys Thr Gly Ile Ser Thr Asp Cys Pro Arg Asn Arg Tyr Lys Gly
 50                  55                  60

Lys Glu Asp
 65

<210> SEQ ID NO 4
<211> LENGTH: 11
<212> TYPE: PRT
<213> ORGANISM: Echis carinatus

<400> SEQUENCE: 4

Lys Arg Ala Arg Gly Asp Asp Met Asp Asp Tyr
 1               5                  10

<210> SEQ ID NO 5
<211> LENGTH: 11
<212> TYPE: PRT
<213> ORGANISM: Echis carinatus

<400> SEQUENCE: 5

Lys Arg Ala Val Gly Asp Asp Val Asp Asp Tyr
 1               5                  10

<210> SEQ ID NO 6
<211> LENGTH: 11
<212> TYPE: PRT
<213> ORGANISM: Echis carinatus

<400> SEQUENCE: 6

Lys Arg Ala Met Leu Asp Gly Leu Asn Asp Tyr
 1               5                  10

<210> SEQ ID NO 7
<211> LENGTH: 64
<212> TYPE: PRT
<213> ORGANISM: Vipera lebetina
```

```
<400> SEQUENCE: 7

Asn Ser Gly Asn Pro Cys Cys Asp Pro Val Thr Cys Gln Pro Arg Arg
  1               5                  10                  15

Gly Glu His Cys Val Ser Gly Lys Cys Cys Arg Asn Cys Lys Phe Leu
             20                  25                  30

Arg Ala Gly Thr Val Cys Lys Arg Ala Val Gly Asp Asp Met Asp Asp
         35                  40                  45

Tyr Cys Thr Gly Ile Ser Ser Asp Cys Pro Arg Asn Pro Tyr Lys Asp
     50                  55                  60

<210> SEQ ID NO 8
<211> LENGTH: 49
<212> TYPE: PRT
<213> ORGANISM: Eristocophis macmahonii

<400> SEQUENCE: 8

Gln Glu Glu Pro Cys Ala Thr Gly Pro Cys Cys Arg Arg Cys Lys Phe
  1               5                  10                  15

Lys Arg Ala Gly Lys Val Cys Arg Val Ala Arg Gly Asp Trp Asn Asp
             20                  25                  30

Asp Tyr Cys Thr Gly Lys Ser Cys Asp Cys Pro Arg Asn Pro Trp Asn
         35                  40                  45

Gly

<210> SEQ ID NO 9
<211> LENGTH: 49
<212> TYPE: PRT
<213> ORGANISM: Echis carinatus

<400> SEQUENCE: 9

Glu Cys Glu Ser Gly Pro Cys Cys Arg Asn Cys Lys Phe Leu Lys Glu
  1               5                  10                  15

Gly Thr Ile Cys Lys Arg Ala Arg Gly Asp Asp Met Asp Asp Tyr Cys
             20                  25                  30

Asn Gly Lys Thr Cys Asp Cys Pro Arg Asn Pro His Lys Gly Pro Ala
         35                  40                  45

Thr

<210> SEQ ID NO 10
<211> LENGTH: 70
<212> TYPE: PRT
<213> ORGANISM: Trimeresurus flavoviridis

<400> SEQUENCE: 10

Gly Glu Glu Cys Asp Cys Gly Ser Pro Ser Asn Pro Cys Cys Asp Ala
  1               5                  10                  15

Ala Thr Cys Lys Leu Arg Pro Gly Ala Gln Cys Ala Asp Gly Leu Cys
             20                  25                  30

Cys Asp Gln Cys Arg Phe Lys Lys Lys Thr Gly Ile Cys Arg Ile Ala
         35                  40                  45

Arg Gly Asp Phe Pro Asp Asp Arg Cys Thr Gly Leu Ser Asn Asp Cys
     50                  55                  60

Pro Arg Trp Asn Asp Leu
 65                  70

<210> SEQ ID NO 11
<211> LENGTH: 68
<212> TYPE: PRT
```

<213> ORGANISM: Calloselasma rhodostoma

<400> SEQUENCE: 11

Gly Lys Glu Cys Asp Cys Ser Ser Pro Glu Asn Pro Cys Cys Asp Asp
1               5                   10                  15

Ala Thr Cys Lys Leu Arg Pro Gly Ala Gln Cys Gly Glu Gly Leu Cys
                20                  25                  30

Cys Glu Gln Cys Lys Phe Ser Arg Ala Gly Lys Ile Cys Arg Ile Pro
            35                  40                  45

Arg Gly Asp Met Pro Asp Asp Arg Cys Thr Gly Gln Ser Ala Asp Cys
        50                  55                  60

Pro Arg Tyr His
65

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Gly Arg Gly Asp Ser Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Gly Arg Gly Glu Ser Pro
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Met Leu Asp Gly
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Arg Gly Asp Ser
1

<210> SEQ ID NO 16
<211> LENGTH: 13
<212> TYPE: PRT

```
<213> ORGANISM: Artificial Sequence
<220> FEATURE:
<223> OTHER INFORMATION: Description of Artificial Sequence: synthetic
      peptide
<221> NAME/KEY: DISULFID
<222> LOCATION: (1)..(13)

<400> SEQUENCE: 16

Cys Lys Arg Ala Met Leu Ala Gly Leu Asn Asp Tyr Cys
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: synthetic
      peptide
<221> NAME/KEY: DISULFID
<222> LOCATION: (1)..(13)

<400> SEQUENCE: 17

Cys Lys Arg Ala Met Leu Asp Gly Leu Asn Asp Tyr Cys
 1               5                  10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Met Leu Asp Gly Leu
 1               5

<210> SEQ ID NO 19
<211> LENGTH: 67
<212> TYPE: PRT
<213> ORGANISM: Echis carinatus
<220> FEATURE:
<221> NAME/KEY: VARIANT
<222> LOCATION: (33)
<223> OTHER INFORMATION: R or N
<221> NAME/KEY: VARIANT
<222> LOCATION: (37)
<223> OTHER INFORMATION: V or I
<221> NAME/KEY: VARIANT
<222> LOCATION: (64)
<223> OTHER INFORMATION: G or D
<221> NAME/KEY: VARIANT
<222> LOCATION: (66)
<223> OTHER INFORMATION: E or D

<400> SEQUENCE: 19

Asn Ser Val His Pro Cys Cys Asp Pro Val Lys Cys Glu Pro Arg Glu
 1               5                  10                  15

Gly Glu His Cys Ile Ser Gly Pro Cys Cys Arg Asn Cys Tyr Phe Leu
            20                  25                  30

Xaa Ala Gly Thr Xaa Cys Lys Arg Ala Val Gly Asp Asp Val Asp Asp
        35                  40                  45

Tyr Cys Ser Gly Ile Thr Pro Asp Cys Pro Arg Asn Arg Tyr Lys Xaa
    50                  55                  60

Lys Xaa Asp
65
```

-continued

```
<210> SEQ ID NO 20
<211> LENGTH: 67
<212> TYPE: PRT
<213> ORGANISM: Echis carinatus
<220> FEATURE:
<221> NAME/KEY: VARIANT
<222> LOCATION: (11)
<223> OTHER INFORMATION: K or T
<221> NAME/KEY: VARIANT
<222> LOCATION: (40)
<223> OTHER INFORMATION: R or K
<221> NAME/KEY: VARIANT
<222> LOCATION: (55)
<223> OTHER INFORMATION: T or S

<400> SEQUENCE: 20

Asn Ser Val His Pro Cys Cys Asp Pro Val Xaa Cys Glu Pro Arg Glu
  1               5                  10                  15

Gly Glu His Cys Ile Ser Gly Pro Cys Cys Arg Asn Cys Lys Phe Leu
             20                  25                  30

Asn Ala Gly Thr Ile Cys Lys Xaa Ala Met Leu Asp Gly Leu Asn Asp
         35                  40                  45

Tyr Cys Thr Gly Ile Ser Xaa Asp Cys Pro Arg Asn Arg Tyr Lys Gly
     50                  55                  60

Lys Glu Asp
 65
```

EC-3, AN INHIBITOR OF α4β1 AND α4β7 INTEGRINS

CROSS-REFERENCE TO RELATED APPLICATIONS

This application claims the benefit of U.S. Provisional Application Ser. No. 60/055,825, filed 15 Aug. 1997, and U.S. Provisional Application Ser. No. 60/055,957, filed 18 Aug. 1997.

REFERENCE TO GOVERNMENT GRANT

The invention described herein was made, in part, in the course of work supported by the National Institutes of Health under Grant Nos. HL 45486 and HL 19055. The government has certain rights in the invention.

FIELD OF THE INVENTION

This invention generally relates to methods and compositions for modulating cell adhesion and for inhibiting the interaction between integrins and their ligands. In particular, the invention relates to peptides that selectively inhibit α4 integrins.

BACKGROUND OF THE INVENTION

A. Integrins

Integrins are a family of cell surface proteins that mediate adhesion between cells (cell-cell adhesion) and between cells and extracellular matrix proteins (cell-ECM adhesion). Integrins are heterodimeric structures composed of noncovalently bound α and β subunits. In humans there are at least 15 different α and eight different β subunits, and these can combine to form proteins with diverse biological activities and ligand specificities.

The integrins play important roles in many diverse biological processes including platelet aggregation, tissue repair, angiogenesis, bone destruction, tumor invasion, inflammation, and immune reactions. The integrins are, therefore, important targets for therapeutic intervention in human disease.

Integrin αIIbβ3 (glycoprotein IIb/IIIa complex) binds fibrinogen on the platelet surface and mediates platelet aggregation. Integrin αvβ3 is predominantly expressed on endothelial cells and plays an important role in angiogenesis. Integrin αvβ3 is also expressed on osteoclasts and participates in bone destruction. Integrin α5β1 is widely distributed on a variety of cells; it plays a critical role in cell adhesion to extracellular matrix as well as in the formation of tissues and organs during embryonic development. All three integrins αIIbβ3, αvβ3 and α5β1 recognize RGD sequences in the adhesive ligands.

One example of the therapeutic targeting of integrins is the use of integrin inhibitors as antithrombotic agents. Peptides and peptidomimetics that block the adhesion of GPIIb/IIIa to fibrinogen can prolong bleeding times and prevent thrombotic occlusion in vivo. One group of naturally occurring peptides that inhibit platelet aggregation by interfering with fibrinogen binding to GPIIb/IIIa has been called the "disintegrins."

B. Disintegrins

The disintegrins are a family of low molecular weight cysteine-rich peptides that have been isolated from the venom of various snakes (reviewed in Niewiarowski et al., *Seminars in Hematology* 31(4):289–300 (1994)). Most disintegrins described to date contain an RGD motif. RGD is a recognition site for many integrins, and disintegrins inhibit fibrinogen binding to GPIIb/IIIa, as well as the binding of other ligands to RGD-dependant integrins on the surface of cells. Peptides modeled on the structure of disintegrins have potential clinical applications in the prevention and treatment of coronary thrombosis, stroke, and other vascular diseases.

The first disintegrin described in the literature, trigramin, was identified and characterized on the basis of its ability to block platelet aggregation and inhibit fibrinogen binding to αIIbβ3. Trigramin contains 72 amino acids including 12 cysteines, is linked by S-S bonds, and contains an RGD sequence. Subsequently several other RGD containing viper venom disintegrins of similar size were isolated.

A 49 amino acid disintegrin, called echistatin, has been isolated from the venom of *Echis carinatus* (Gan et al., *J. Biol. Chem.* 263:19827–32 (1988)). Like other disintegrins, echistatin contains an RGD sequence and inhibits GPIIb/IIIa binding of fibrinogen. Echistatin has been called a "promiscuous disintegrin" because it blocks αIIbβ3, αvβ3 and α5β1 with similar potency.

NMR studies on RGD-containing disintegrins shows that the RGD sequence is located in a mobile loop joining two strands of β sheet protruding from the protein core (reviewed in Niewiarowski et al., *Semin. Hematol.* 31:289–300 (1994)). The disulfide bonds around the RGD sequence maintain the hair-pin loop conformation in each peptide, and this conformation seems to be important for potency and selectivity.

The disintegrin eristostatin, originally described as a potent inhibitor of αIIbβ3, also inhibits human melanoma cell (MV3) metastases in immune deficient mice. It has been suggested that this effect is mediated by altering the function of an α4 integrin expressed on MV3 cells (Danen et al, *Exp. Cell Res.* 238:188-196 (1998)).

C. The α4 Integrins

The α4 integrins, α4β1 and α4β7, are expressed on leukocytes and lymphoid cells, and play a major role in inflammation and auto-immune diseases.

The α4β1 integrin (which has also been called VLA4, very late activation antigen 4) mediates cell adhesion to vascular cell adhesion molecule-1 (VCAM-1), an adhesive molecule belonging to the IgG superfamily which is expressed on endothelial cells at sites of inflammation. The integrin α4β1 also binds to alternatively spliced variants of fibronectin containing connecting segment 1 (CS-1).

The α4β7 integrin binds to the gut homing receptor mucosa addressin cell adhesion molecule-1 (MadCAM-1) and to a lesser extent to CS-1 and VCAM-1.

Cytokine activated leukocytes express α4β1 and α4β7 integrins. Interaction of these integrins with VCAM-1 or MadCAM-1 (which are also up-regulated by cytokines) on endothelium mediates capillary infiltration by leukocytes, which can lead to tissue and organ destruction. Selectins and β2 integrins also contribute to this process. Altevost et al. reported that the α4 subunit itself is a ligand for α4β1 and α4β7 integrins (*J. Exp. Med.* 182:345–55 (1995)), suggesting that α4 integrins may play a role in leukocyte communication during the immune response.

Activation and up-regulation of α4β1 or α4β7 on lymphocytes or macrophages is believed to play a significant role in the progression of many disease states, including insulin dependent diabetes mellitus, multiple sclerosis, rheumatoid arthritis, ulcerative colitis, arteriosclerosis, asthma, allergy, organ rejection, and restenosis of arteries after surgery or angioplasty. The α4 integrins are therefore targets for therapeutic intervention in a variety of inflammatory, auto-immune, and other diseases.

D. The α4 Integrins as Therapeutic Targets

There are several animal models of inflammatory and autoimmune diseases in which endothelial infiltration by lymphocytes and organ destruction are blocked by anti-α4 monoclonal antibodies. As an example, anti-α4 antibody inhibits lymphocyte infiltration of Langerhans islets in NOD mice, thus preventing development of spontaneous insulin dependent diabetes (Yang et al., *Proc. Natl. Acad. Sci. USA* 4 91:12604–08 (1994)). Anti-α4 monoclonal antibodies have also shown in vivo efficacy in animal models of asthma (Abraham et at., *J. Clin. Invest.* 93:776 (1994)), multiple sclerosis (Yednock et al., *Nature* 356:63 (1992)), inflammatory bowel disease (Podoisky et al., *J. Clin. Invest.* 92:372 (1993)), contact hypersensitivity (Chisholm et al., *Eur. J. Immunol.* 23:682 (1993)), and cardiac allograft rejection (Isobe et al., *J. Immunol.* 153:5810 (1994)).

There have been several attempts to isolate naturally occurring or to develop synthetic inhibitors of α4β7 and α4β1. Synthetic inhibitors that have been reported include cyclic RGD peptides and short peptides based on the sequences of MadCAM-1, VCAM-1, and CS-1. These peptides are typically active in vitro at the micromolar level.

Molossi et al. (*J. Clin. Invest.* 95:2601–10 (June 1995)) reported that blockade of α4β1 (VLA-4) integrin binding to fibronectin with CS-1 peptide reduces accelerated coronary arteriopathy in rabbit cardiac allografts. The sequence of the CS-1 peptide was phenylacetic acid-Leu-Asp-Phe-d-Pro-amide.

Kogan et al. (WO 96100581) reported that cyclic peptides modeled after a portion of the CS-1 peptide inhibited the binding of α4β1 integrin to VCAM-1 at concentrations of peptide less than about 10 μM.

Kogan et al. (U.S. Pat. No. 5,510,332) reported that a peptide comprising the LDV domain of CS-1 peptide inhibited the binding of α4β1 integrin to VCAM-1 with an $IC_{50}$ of 30 μM.

Shroff et al. (*Bioorganic and Medicinal Chemistry Letters* 6(21):2495–2500 (1996)) reported a series of peptides based on the N-terminal domain of MAdCAM-1 inhibited the binding of HUT78 cells activated with $Mn^{++}$ to MAdCAM-1 with an $IC_{50}$ of 5 to >1000 μM. Cyclic peptides based on an N-terminal conserved motif in VCAM-1 have also been reported to inhibit VCAM/α4β1 mediated leukocyte adhesion (Wang et al., *Proc. Natl. Acad. Sci. USA* 92:5714 (1995)).

Cyclic RGDS (SEQ ID NO:15) peptides have been reported as strong inhibitors of α4β1 and α4β7 integrins (Cardarelli et al., *J. Biol. Chem.* 269:18668–73 (1994); Yang et al. *Eur. J. Immunol.* 28:995–1004 (1998)).

Vanderslice et al. (*J. Immunol.* 158:1710–18 (1997)) recently reported that a cyclic peptide based on the LDV sequence of CS-1 inhibited α4β1 dependent binding of lymphocytes to VCAM and CS-1 with an $IC_{50}$ of 1–3 μM.

There is a need for potent and specific inhibitors of α4 integrins, and for methods of specifically inhibiting the binding of α4 integrins to cellular ligands.

SUMMARY OF THE INVENTION

The present invention relates to the discovery of the EC-3 protein, a heterodimeric disintegrin that is an extremely potent antagonist of α4 integrins. EC-3 proteins and peptides inhibit adhesion of cells expressing α4 integrins in an RGD-independent manner.

The invention provides a substantially purified EC-3 protein, isolated from *E. carinatus* venom and characterized by: (a) an apparent molecular weight of about 14,762 Da, as determined by electrospray ionization mass spectrometry; (b) elution from a C-18 HPLC column at about 40% acetonitrile; and (c) the ability to inhibit adhesion of Jurkat cells to VCAM-1.

The invention also provides a substantially purified EC-3A peptide, isolated from EC-3 protein which has been reduced and alkylated, and characterized by: (a) a molecular mass of about 8478 Da in its ethylpyridylated form, as determined by electrospray ionization mass spectrometry; (b) elution from a C-18 HPLC column at about 42% acetonitrile; and (c) the ability to inhibit adhesion of K562 cells to fibronectin.

The invention further provides a substantially purified EC-3B peptide, isolated from EC-3 protein which has been reduced and alkylated with vinylpyridine, and characterized by: (a) a molecular mass of about 7950 Da in its carboxymethylated form, as determined by electrospray ionization mass spectrometry; (b) elution from a C-18 HPLC column at about 46% acetonitrile; and (c) the ability to inhibit adhesion of Jurkat cells to VCAM-1.

One preferred embodiment of the invention is a substantially purified EC-3A peptide comprising the sequence SEQ ID NO:19, or a biologically active fragment or derivative thereof. A more preferred embodiment is a substantially purified peptide comprising the sequence SEQ ID NO:2, or a biologically active fragment or derivative thereof.

Another preferred embodiment of the invention is a substantially purified EC-3B peptide comprising the sequence SEQ ID NO:20, or a biologically active fragment or derivative thereof. A more preferred embodiment is a substantially purified peptide comprising the sequence SEQ ID NO:3, or a biologically active fragment or derivative thereof.

A further embodiment of the invention is a substantially purified EC-3 protein comprising two subunits, wherein one subunit comprises the sequence SEQ ID NO:19 or a biologically active fragment or derivative thereof and one subunit comprises the sequence SEQ ID NO:20 or a biologically active fragment or derivative thereof.

The invention is also directed to a biologically active peptide fragment of EC-3B having the sequence X-Y-Met-Leu-Asp-Z, where X is H or a blocking group, Y is zero or more amino acids, and Z is OH or zero or more amino acids. In some preferred embodiments the biologically active peptide is from about 3 to about 20 amino acids. In a more preferred embodiment the peptide has the sequence SEQ ID NO:16. In another more preferred embodiment the peptide has the sequence SEQ ID NO:14.

Another aspect of the invention is a substantially purified nucleic acid encoding a protein or peptide according to the invention. One embodiment of the invention is a vector comprising a nucleic acid encoding a protein or peptide according to the invention. Another embodiment of the invention is a recombinant cell comprising a nucleic acid encoding a protein or peptide according to the invention.

The invention further provides an antibody which specifically binds to a protein or peptide according to the invention. The antibody may be a monoclonal antibody or a polyclonal antibody or an antibody fragment that is capable of binding antigen. One aspect of the invention is a hybridoma that produces a monoclonal antibody which specifically binds to a protein or peptide according to the invention.

Another aspect of the invention is a substantially purified echistatin polypeptide in which the Arg-Gly-Asp residues at positions 24–26 are replaced by Met-Leu-Asp, or a biologically active fragment or derivative thereof.

The invention further provides a method of isolating a peptide that binds to an integrin of interest from venom comprising: (a) dissolving venom in a solvent, (b) centrifuging the dissolved venom to remove high molecular weight proteins, (c) fractionating the supernatant from step (b), (d) immobilizing the fractions from step (c) on a solid support, (e) adding detectably labeled cells which express the integrin of interest to the immobilized fractions, (f) detecting the number of cells bound to each immobilized fraction, and (g) isolating peptide from those fractions which showed enhanced cell binding in step (f).

Another aspect of the invention is a composition comprising a pharmaceutically acceptable carrier and a protein, peptide, or nucleic acid according to the invention.

The invention encompasses a method of inhibiting the binding of an α4 integrin to VCAM-1 comprising contacting a cell that expresses the α4 integrin with an effective amount of a protein or peptide according to the invention. In preferred embodiments the integrin is α4β1 or α4β7.

The invention also encompasses a method of inhibiting the binding of α4β7 integrin to MadCAM-1 comprising contacting a cell that expresses α4β7 with an effective amount of a protein or peptide according to the invention.

The invention further encompasses a method of inhibiting the binding of an α4 integrin to CS-1 comprising contacting a cell that expresses the α4 integrin with an effective amount of a protein or peptide according to the invention.

One preferred embodiment of the invention is a method of inhibiting the interaction between cells expressing an α4 integrin and VCAM-1 in a patient in need of such treatment comprising administration of a therapeutically effective amount of a composition comprising a pharmaceutically acceptable carrier and a protein or peptide according to the invention.

Another preferred embodiment of the invention is a method of inhibiting the interaction between cells expressing an α4 integrin and MadCAM-1 in a patient in need of such treatment comprising administration of a therapeutically effective amount of a composition comprising a pharmaceutically acceptable carrier and a protein or peptide according to the invention.

A further preferred embodiment of the invention is a method of, inhibiting the interaction between cells expressing an α4 integrin and CS-1 in a patient in need of such treatment comprising administration of a therapeutically effective amount of a composition comprising a pharmaceutically acceptable carrier and a protein or peptide according to the invention.

The invention is also directed to the use of a protein, peptide, or nucleic acid according to the invention for the preparation of a medicament for inhibiting the interaction between cells expressing an α4 integrin and its ligands.

Other aspects and advantages of the present invention are described in the drawings and in the following detailed description of the preferred embodiments thereof.

DESCRIPTION OF THE DRAWINGS

FIG. 4 shows the amino acid sequences of EC-3 subunits EC-3A (SEQ ID NOs:19 and 2.

FIG. 5 shows a comparison of the amino acid sequence of EC3A (SEQ ID NO:2), EC3B (SEQ ID NO:3), with two short disintegrins eristostatin (SEQ ID NO:8) and echistatin (SEQ ID NO:9), with two medium size disintegrins flavoridin (SEQ ID NO:10) and kistrin (SEQ ID NO:11), and with a disintegrin domain of Le3 (SEQ ID NO:7), a metallproteinase from Vipera lebetina venom. Boxes show the positions of conserved cysteine residues. The typical active site of the disintegrins (RGD) as well as the corresponding position in EC-3A(VGD), EC-3B (MLD), and Le3 (VGD) are underlined.

FIG. 9 shows the effect of RGD peptides and HP2/1 on Jurkat cell-EC-3 interactions.

DETAILED DESCRIPTION OF THE INVENTION

Figure 1:
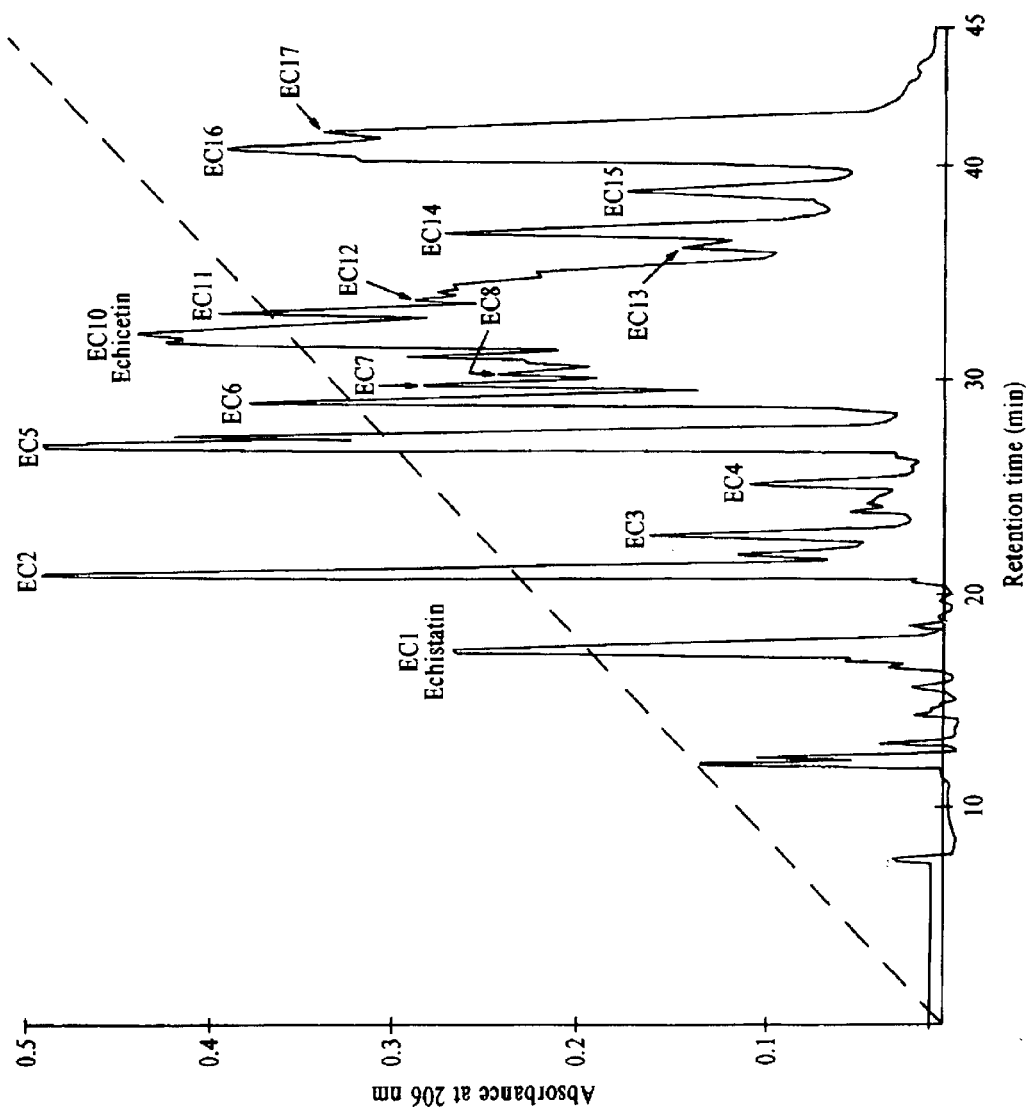
FIG. 1 shows the HPLC fractionation of *E. carinatus* venom on a reverse phase C-18 HPLC column eluted with an acetonitrile gradient (dashed line). Fractions containing the disintegrin echistatin (EC1), the echicetin protein (which binds to GPIb/IX receptors on platelets, EC10) and EC3 are indicated.

The present invention relates to the discovery of a novel protein, EC-3, which is a potent inhibitor of α4β1 and α4β7 integrins. The EC-3 protein was purified from *Echis carinatus suchoreki* viper venom. EC-3 inhibits adhesion of cells expressing α4β1 and α4β7 integrins to natural ligands VCAM-1 and MadCAM-1 with $IC_{50}$=5–300 nM. Its blocking activity resembles that of some monoclonal antibodies but is 2 to 3 orders of magnitude higher than most synthetic antagonists. The EC-3 inhibitory effect is not RGD dependent but is competed by HP 2/4 and HP 2/1 monoclonal antibodies, which recognize epitopes on α4.

EC-3 comprises two types of subunits, EC-3A and EC-3B, which are covalently linked. The EC-3A and EC-3B subunits show a high degree of homology with other viper venom disintegrins, including the alignment of conserved cysteines. The conserved RGD motif of integrins is replaced, however, by VGD in EC-3A and by MLD in EC-3B.

A. Abbreviations and Short Forms

The following abbreviations and short forms are used in this specification.

"BSA" is bovine serum albumin.
"CHO cells" are Chinese hamster ovary cells.
"CMFDA" is 5-chloromethylfluorescein diacetate.
"CS-1" is connecting segment 1 of fibronectin.
"DBA" is direct binding assay.
"EC-3 protein" (also called EC3 protein) is a heterodimeric protein comprising an EC-3A (also called EC3A) subunit and an EC-3B (also called EC3B) subunit. The term "EC-3 peptide" (also called EC3 peptide) as used herein encompasses the EC-3 protein as well as the EC-3A and EC-3B subunits, and fragments thereof.
"ECM" is extracellular matrix.
"ep" is ethylpyridylethylated. The ethylpyridylethylated forms of EC-3A and EC-3B are designated "epEC3A" and "epEC3B."
"HBSS" is Hanks' balanced salt solution.
"HPLC" is high performance liquid chromatography.
"Ig" is immunoglobulin.
"$IC_{50}$" is the concentration of a biologically active agent such as a peptide, which inhibits 50% of the activity obtained in the absence of the agent.
"Mab" is monoclonal antibody.
"MadCAM-1" is mucosal addressin cell adhesion molecule-1, a member of the IgG protein superfamily having a mucin component. MadCAM-1 is a cellular ligand for the α4β7 integrin.
"MLD" is the one letter designation of the amino acid sequence Met-Leu-Asp, which occurs in the EC-3 protein.
"NOD mouse" is a Non Obese Diabetic mouse.
"PBS" is phosphate buffered saline solution.
"RGD" is the one letter designation for the amino acid sequence Arg-Gly-Asp. RGD is a recognition site for many disintegrins. A related recognition site is "KGD" which is the one letter designation for Lys-Gly-Asp.
"TFA" is trifluoroacetic acid.
"VCAM-1" is vascular cell adhesion molecule-1, a member of the IgG protein superfamily which is a cellular ligand for the α4β1) and α4β7 integrins.
"VLA-4" is very late activation antigen 4.

B. Definitions

The following definitions, of terms used throughout the specification, are intended as an aid to understanding the scope and practice of the present invention.

A "peptide" is a compound comprised of amino acid residues covalently linked by peptide bonds. Amino acids have the following general structure:

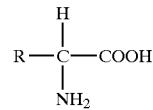

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. Peptides comprising a large number of amino acids are sometimes called "polypeptides". The EC-3A and EC-3B subunits of EC-3 are peptides.

A "protein" is a polypeptide which plays a structural or functional role in a biological system. Proteins comprise one or more peptides. EC-3 is a protein.

"Fibrinogen" is a blood plasma glycoprotein, which is involved in platelet aggregation and fibrin formation.

"Integrins" are a family of heterodimeric cell surface proteins which mediate adhesion between cells and between cells and extracellular matrix proteins.

"Disintegrins" are a family of peptides isolated from snake venoms which inhibit the binding of various ligands to integrins.

"Echistatin" is a 49 amino acid disintegrin isolated from *Echis carinatus* venom.

"Homology" means similarity of sequence reflecting a common evolutionary origin. Peptides or proteins are said to have homology, or similarity, if a substantial number of their amino acids are either (1) identical, or (2) have a chemically similar R side chain. Nucleic acids are said to have homology if a substantial number of their nucleotides are identical.

"Substantial amino acid sequence homology" means an amino acid sequence homology greater than about 30 percent, preferably greater than about 60%, more preferably greater than about 80%, and most preferably greater than about 90 percent.

"Substantially purified peptide" or "substantially purified protein" means a peptide or protein which is substantially free of those compounds that are normally associated therewith in its natural state (e.g., other proteins or peptides, nucleic acids, carbohydrates, lipids). "Substantially purified" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "biologically active fragment" of an EC-3 peptide is a fragment derived from an EC-3 peptide which retains at least one biological activity of the EC-3 peptide.

A "biologically active derivative" of an EC-3 peptide is any analogue, variant, derivative, or mutant which is derived from an EC-3 peptide, which has substantial amino acid sequence homology with the EC-3 peptide, and which retains at least one biological property of the EC-3 peptide. Different variants of EC-3 peptides may exist in nature. These variants may be allelic variations characterized by differences in the nucleotide sequences of the structural gene coding for EC-3 peptides, or may involve differential splicing or post-translational modification. The skilled artisan can produce derivatives having single or multiple amino acid substitutions, deletions, additions, or replacements. These derivatives may include, inter alia: (a) derivatives in which one or more amino acid residues are substituted with conservative or non-conservative amino acids, (b) derivatives in which one or more amino acids are added to an EC-3 peptide, (c) derivatives in which one or more of the amino acids includes a substituent group, and (d) derivatives in which the EC-3 peptide is fused with another peptide such as serum albumin. The techniques for obtaining these derivatives, including genetic (suppressions, deletions, mutations, etc.), chemical, and enzymatic techniques, are known to persons having ordinary skill in the art.

Biologically active fragments and biologically active derivatives of EC-3 peptides are intended to be included within the scope of this invention.

A "blocking group" is any group capable of blocking the N-terminal amino group of a peptide. A preferred blocking group is an alkyl group; a most preferred blocking group is an acetyl group.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence.

"Isolated nucleic acid" means a nucleic acid which is substantially free of those compounds that are normally associated therewith in its natural state. "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

The phrase "a nucleic acid which hybridizes at high stringency" means that the hybridized nucleic acids are able to withstand a washing under high stringency conditions. An example of high stringency washing conditions for DNA-DNA hybrids is 0.1×SSC, 0.5% SDS at 68° C. Other conditions of high stringency washing are known to persons having ordinary skill in the art.

"Regulatory region" means a nucleic acid sequence which regulates the expression of a nucleic acid. A regulatory region may include sequences which are naturally responsible for expressing a particular nucleic acid. (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"Operatively linked to a regulatory region" means that the peptide or polypeptide coding region is connected to transcriptional and translational regulatory sequences in such a way as to permit polypeptide expression when the appropriate molecules (such as activator proteins and polymerases) are present in a cell or cell free system.

A "vector" is any means for the transfer of a nucleic acid according to the invention into a host cell. The term "vector" includes both viral and nonviral means for introducing the nucleic acid into a prokaryotic or eukaryotic cell in vitro, ex vivo, or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

A "recombinant cell" is a cell which contains a nucleic acid which is not naturally present in the cell. "Recombinant cell" includes higher eukaryotic cells such as mammalian cells, lower eukaryotic cells such as yeast cells, prokaryotic cells, and archaebacterial cells.

"Antibody" as used herein includes monoclonal and polyclonal antibodies as well as fragments capable of binding antigen, including but not limited to Fab and $F(ab)_2$ fragments.

"Pharmaceutically acceptable carrier" includes diluents and fillers which are pharmaceutically acceptable for methods of administration, may be sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

C. Proteins and Peptides

The present invention provides substantially purified EC-3 peptides, including the EC-3 protein, the EC-3A and EC-3B peptides, and biologically active fragments and derivatives of EC-3, EC-3A, and EC-3B. The invention also provides methods of isolation and peptides isolated from other venoms having biological activity similar to EC-3.

The peptides of the present invention may be recombinant peptides, natural peptides, or synthetic peptides. Each peptide is characterized by a reproducible single molecular weight and/or multiple set of molecular weights, chromatographic response and elution profile, amino acid composition and sequence, and biological activity.

The peptides of the present invention may be isolated from natural sources, such as viper venom, using the methods disclosed herein.

The peptides of the invention may also be chemically synthesized, using, for example, solid phase synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group of the t-butyloxycarbonyl group, various coupling reagents (e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures. See Merrifield, *J. Amer. Chem. Soc.* 85:2149–54 (1963) and *Science* 50: 178–85 (1965). Additional information about the solid phase synthesis procedure can be had by reference to the treatise by Steward and Young ("Solid Phase Peptide Synthesis," W. H. Freeman & Co., San Francisco, 1969, and the review chapter by Merrifield in *Advances in Enzymology* 32:221–296, F. F. Nold, Ed., Interscience Publishers, New York, 1969; and Erickson and Merifield, *The Proteins* 2:255 et seq. (ed. Neurath and Hill), Academic Press, New York, 1976. The synthesis of peptides by solution methods is described in Neurath et al., eds. (*The Proteins*, Vol. II, 3d Ed., Academic Press, NY (1976)).

Crude peptides may be purified using preparative HPLC. The amino terminus may be blocked according, for example, to the methods described by Yang et al. (*FEBS Left.* 272:61–64 (1990)).

Peptide synthesis includes both manual and automated techniques employing commercially available peptide synthesizers. Fragments and derivatives of EC-3 peptides may be prepared by chemical synthesis and biological activity can be tested using the methods disclosed herein.

Alternatively, the peptides of the invention may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered.

In some embodiments, the peptides of the present invention may be used in the form of a pharmaceutically acceptable salt.

Suitable acids which are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

D. Nucleic Acids

The present invention provides substantially purified nucleic acids which encode peptides according to the invention.

The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Sambrook (*Molecular Cloning*, Cold Spring Harbor Laboratories, Second Ed., 1989), and in Ausubel (*Current Protocols in Molecular Biology*, Wiley and Sons, 1987), which are incorporated by reference.

Having the EC-3A and EC-3B amino acid sequences disclosed herein, one of skill in the art can isolate or prepare a gene that encodes the peptide of interest. Synthetic genes may be synthesized directly on a DNA synthesizer, or may be synthesized as complementary oligonucleotides which are ligated together to form the synthetic gene. Alternatively, the native gene encoding the peptides of the invention may be isolated from genomic or cDNA libraries. As an example, based upon the amino acid sequences disclosed herein, one of skill in the art can prepare suitable oligonucleotide probes and polymerase chain reaction (PCR) primers, which can be used to screen a cDNA library prepared from *E. carinatus* venom glands. Positive clones are purified and sequenced to confirm their identity.

The nucleic acids encoding EC-3 peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate to be immunized. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lacI, lacZ, T3, T7, lambda $P_r$, $P_l$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, Ela, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include but are not limited to SV40 polyadenylation signals and LTR polyadenylation signals.

Fragments and derivatives of EC-3 peptides may be prepared using recombinant DNA technology. The biological activity of the fragments and derivatives can be assayed using the methods disclosed herein.

E. Antibodies

The present invention provides antibodies against EC-3 peptides. These antibodies may be monoclonal antibodies or polyclonal antibodies. The present invention includes chimeric, single chain, and humanized antibodies, as well as Fab fragments and the products of an Fab expression library.

Polyclonal antibodies may be generated against the intact protein or peptide, or against a fragment, derivative, or epitope of the protein or peptide. Antibodies may be obtained following the administration of the protein, polypeptide, fragment, derivative, or epitope to an animal, using the techniques and procedures known in the art.

Monoclonal antibodies may be prepared using the method of Mishell, B. B., et al., *Selected Methods In Cellular*

*Immunology*, (W. H. Freeman, ed.) San Francisco (1980). Briefly, a peptide of the present invention is used to immunize spleen cells of Balb/C mice. The immunized spleen cells are fused with myeloma cells. Fused cells containing spleen and myeloma cell characteristics are isolated by growth in HAT medium, a medium which kills both parental cells, but allows the fused products to survive and grow.

Antibodies may be used to purify the peptides according to the invention, using immunoaffinity techniques which are well known by those of skill in the art.

F. Isolation of Related Peptides from Venoms

The present invention provides a method for isolating peptides that bind to an integrin of interest from the venom of snakes or other organisms. This method comprises the steps of:

(a) dissolving venom in a solvent, (b) centrifuging the dissolved venom to remove high molecular weight proteins, (c) fractionating the supernatant from step (b), (d) immobilizing the fractions from step (c) on a solid support, (e) adding detectably labeled cells which express the integrin of interest to the immobilized fractions, (f) detecting the number of cells bound to each immobilized fraction, and (g) isolating peptide from those fractions which showed enhanced cell binding in step (f).

This method may be used to isolate peptides from the venom of species including but not limited to vipers and other snakes including *Agkistrodon acutus, Agkistrodon halys blomhoffi, Agkistrodon contortrix mokasen, Bitis arietans, Bitis caudalis, Bitis gabonica, Bitis g. rhinoceros, Bothrops asper, Bothrops alternata, Bothrops atrox, Bothrops cotiara, Bothrops jararaca, Bothrops newiedi, Bothrops medusa, Bothrops schlegli, Cerastes cerastes, Cerastes vipera, Crotalus adamanteus, C. atrox, C. basilicus, C. durissus totonatacus, C. h. horridus, C. m. molossus, C. ruber, C. scutalatus, C. v. cereberus, C. v. helleri, C. v. lutosus, C. v. oreganus, Echis carinatus sochurecki, Eristicophis macmahoni, Pseudocerastes persicus, Sistrurus m. barbouri, Sistrurus c. terqeminus, Trimeresurus flavoviridis, Trimeresurus gramineus, Vipera lebetina, Vipera ammondytes, Vipera palastinae,* and *Vipera r. russelli,* leeches, ticks, and other organisms.

G. Methods of Treatment

The present invention provides methods of inhibiting the binding of $\alpha 4\beta 1$ or $\alpha 4\beta 7$ integrins to a ligand. A preferred embodiment is a method of inhibiting the interaction between cells expressing $\alpha 4\beta 1$ and/or $\alpha 4\beta 7$ integrins and a ligand, in a patient in need of such treatment, comprising administration of a therapeutically effective amount of a composition comprising one or more peptides according to the invention or a pharmaceutically acceptable salt thereof and a pharmaceutically acceptable carrier. As an example, Non Obese Diabetic mice treated with EC-3 show reduced levels of lymphocyte infiltration in pancreatic islets (see Example 7, below).

Pharmaceutically acceptable carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cystein hydrochloride, ethanol, polyols (propyleneglycol, polyethyleneglycol, glycerol, and the like), vegetable oils (such as olive oil), injectable organic esters such as ethyl oleate, ethoxylated isosteraryl alcohols, polyoxyehtylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

The compositions may be administered by any convenient route which will result in delivery to the blood stream in an amount effective for inhibiting $\alpha 4\beta 1$- and $\alpha 4\beta 7$-mediated adhesion, including orally, rectally, parenterally (intravenously, intramuscularly, intraarterially, or subcutaneously), intracisternally, intravaginally, intraperitoneally, locally (powders, ointments or drops), or as a buccal or nasal spray or aerosol. The compositions can also be delivered through a catheter for local delivery at a target site, or via a biodegradable polymer. The compositions may also be complexed to ligands, or antibodies, for targeted delivery of the compositions.

The compositions are most effectively administered parenterally, preferably intravenously. For intravenous administration, they may be dissolved in any appropriate intravenous delivery vehicle containing physiologically compatible substances, such as sodium chloride glycine, and the like, having a buffered pH compatible with physiologic conditions. Such intravenous delivery vehicles are known to those skilled in the art. In a preferred embodiment, the vehicle is a sterile saline solution. If the peptides are sufficiently small (e.g., less than about 8–10 amino acids) other preferred routes of administration are intranasal, sublingual, and the like.

The compositions according to the invention can be administered in any circumstance in which inhibition of $\alpha 4\beta 1$ and $\alpha 4\beta 7$ integrin function is desirable. Disease states which may be treated include but are not limited to diabetes, multiple sclerosis, rheumatoid arthritis, ulcerative colitis, arteriosclerosis, asthma, allergy, autoimmune disorders, transplant rejection, and restenosis of the arteries following surgery or angioplasty. Because the $\alpha 4$ integrins are expressed on various cancer cells, including leukemia, melanomas, lymphomas, and sarcomas, inhibitors of $\alpha 4$ binding can also be useful in the treatment of some forms of cancer.

The amount of peptide administered depends upon the degree of integrin inhibition that is desired. Those skilled in the art will derive appropriate dosages and schedules of administration to suit the specific circumstances and needs of the patient. Typically, dosages are between about 0.001 mg/kg and about 100 mg/kg body weight. In some embodiments dosages are between about 0.01 mg/kg and about 10 mg/kg body weight. In some embodiments dosages are between about 0.05 mg/kg and about 5 mg/kg body weight.

EXAMPLES

The following examples illustrate the invention. These examples are illustrative only, and do not limit the scope of the invention.

Example 1

Materials and Methods Used in the Examples
A. Materials

Monoclonal antibodies HP2/1 (anti-α4 subunit of VLA-4) and SAM-1 (anti-α5 subunit of VLA-5) were purchased from Immunotech, Inc. (Westbrook, Me.). HP2/4 was received as a gift from Dr. Francisco Sanchez-Madrid (Madrid, Spain). The biological effects of HP2/1 and HP2/4 were identical. Highly purified human fibrinogen was gift from Dr. A. Budzynski (Temple University, Philadelphia Pa.), recombinant human VCAM-1 (Renz et al., *J. Cell Biol.* 125:1395–1406 (1994)) was a gift from Dr. M. Renz (Genentech, San Francisco, Calif.), human vitronectin and fibronectin were purchased from Calbiochem (La Jolla, Calif.) and Sigma (St. Louis, Mo.), respectively. GRGDSP and GRGESP peptides were purchased from Bachem (Torrance, Calif.). RGDS was purchased from Sigma. Highly purified MLDG peptide was kindly provided by Dr. Z. Huang (Thomas Jefferson University, Philadelphia, Pa.). Echistatin was isolated from *Echis carinatus suchoreki* venom as described by McLane et al. (*Biochem. J.* 301:429–436 (1994). Fluorescein isothiocynate (FITC)-conjugated goat anti-mouse IgG for flow cytometry was purchased from Jackson Immune Research (West Grove, Pa.).

A5 and VNRC3 cells, CHO cells transfected with human αIIbβ3 and αvβ3 integrins, respectively (O'Toole et al., *Cell. Regul.* 1:883–893 (1990)), were kindly provided by Dr. M. Ginsberg (Scripps Research Institute, La Jolla, Calif.). CHO cells with deleted α5 integrin (B2 cells) were kindly provided by Dr. R. Juliano (University of North Carolina, Chapel Hill, N.C.). CHO cells transfected with human α4 and its G190A mutant (Kamata et al, *Biochem. J.* 305:945–951 (1995)), and B2 cells transfected with human α4 (α4B2) were kindly provided by dr. Y. Takada (Scripps Research Institute). JY cells expressing α4β7 were a gift of Dr. S. Burakoff (Dana-Farber Cancer Institute, Boston Mass.) K562 cells transfected with α6 integrin were a gift of Dr. A. Sonnenberg (Netherlands Cancer Institute, Amsterdam, Holland). Jurkat cells, K562 cells, and non transfected CHO-K1 cells were purchased from ATCC (Rockville, Md.).
B. Methods Adhesion of cultured cells labeled with 5-chloromethylfluorescein diacetate (CMFDA) was performed as described earlier (Marcinkiewicz et al., *Blood* 90:1565–1575 (1997)). Briefly, ligands (such as EC-3, fibrinogen, vitronectin, fibronectin or VCAM-1) were immobilized on 96-well microtiter plate (Falcon, Pittsburgh, Pa.) in PBS buffer overnight at 4° C. Wells were blocked by 1% BSA in HBSS buffer. Cells were labeled with fluorescein by incubation with 12.5 AM CMFDA in HBSS buffer containing 1% BSA at 37° C. by 15 min. Unbound label was removed by washing with the same buffer. Labeled cells ($1 \times 10^5$ per sample) were added to the well in the presence or absence of inhibitors and incubated at 37° C. for 30 min. Unbound cells were removed by aspiration, the wells were washed and bound cells were lysed by adding 0.5% Triton X-100. In parallel the standard curve was prepared in the same plate from known concentrations of labelled cells. The plate was read using a Cytofluor 2350 fluorescence plate reader (Millipore, Bedford, Mass.) at 485 nm EX(excitation) filter and 530 nm (emmision) filter.

Determination of the molecular mass of native EC-3 or reduced and alkylated EC-3 subunits was done by electrospray ionization mass spectrometry using a Sciex API-III triple quadrupole instrument.

Samples for flow cytometry analysis were prepared as described (Marcinkiewicz et al., *Biochem. J*. 371:118–124 (1996)), and analyzed in a Coulter Epics flow cytometer (Miami, Fla.).

The direct binding assay (DBA) with VCAM-11 g alkaline phosphatase conjugate was performed using Jurkat (α4β1 expressing) and JY (α4β7 expressing) cells according to procedure described in Lobb et al, *Cell Adhes. Commun.* 3:385–398 (1995)).

Example 2

Identification of *Echis carinatus* Venom Fractions Which Inhibit α4β1 Binding to VCAM-1 and α5β1 Binding to Fibronectin Lyophilized *Echis carinatus suchoreki* venom (obtained from Latoxan Serpentarium, Rosans 05150 France) was dissolved in 0.1% trifluoroacetic acid (10 mg/300 μl). The solution was centrifuged for 5 minutes at 5000 rpm to remove the insoluble proteins, and the pellet was discarded. The supernatant was applied to a C-18 HPLC column (250×10 mm, Vydac TPRP equilibrated in 0.1% TFA. The column was eluted with an acetonitrile gradient (0–80% over 45 min.) at a flow rate of 2.0 ml/min. As shown in FIG. 1, the venom separated into 17 main fractions, which were designated "EC1" through "EC17." EC1 was identified as echistatin (Gan et al., *J. Biol. Chem.* 263: 19827–32 (1988)), a strong antagonist of the fibrinogen receptor showing high inhibitory activity ($IC_{50}$=130 nM) in an ADP-induced platelet aggregation assay. EC10 was identified as echicetin (Peng et al., *Blood* 81:2321–28 (1993)). EC-3 eluted at approximately 40% acetonitrile.

Each eluted fraction was lyophilized, then dissolved in water. The protein concentration in each fraction was estimated using the BCA assay (Pierce). Two μg of protein from each fraction were immobilized (in separate wells) on a microtiter plate overnight at 4° C. in PBS (phosphate buffered saline).

Jurkat cells were labeled by incubation with 12.5 μM CMFDA (5-chloromethylfluorescein diacetate) in HBSS (Harks' balanced salt solution) buffer containing 1% BSA (bovine serum albumin) for 15 minutes at 37° C. Cells were washed three times to remove excess CMFDA.

The labeled Jurkat cells were added to the microtiter plate ($1 \times 10^5$ cells per well), and the plate was incubated for 30 minutes at 37° C. After incubation, unbound cells were removed by aspiration and the wells were washed three times with HBSS/BSA buffer.

Bound cells were lysed by the addition of 0.5% Triton X-100, and fluorescence was measured in a Cytofluor 2350 fluorescence plate reader (Millipore) using a 485 nm EX (excitation) filter and a 530 nm EM (emission) filter.

The cells adhered to all fractions except EC4, EC5, and EC8. Fractions with adhesive properties were considered as potential inhibitors of α4β1 binding to VCAM-1 and α5β1 binding to fibronectin.

Figure 2A:
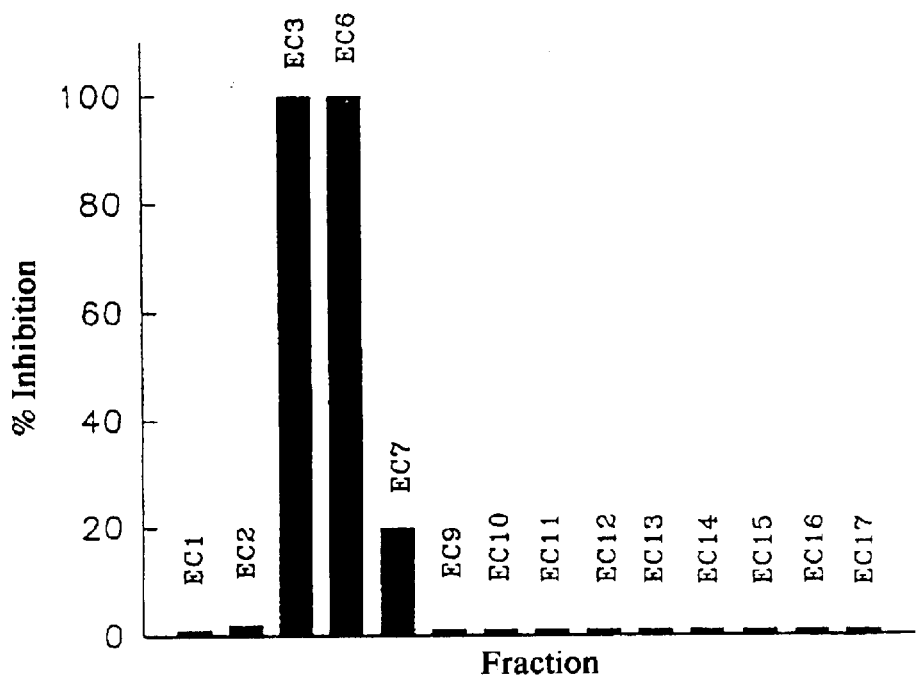
FIG. 2 shows the effect of selected fractions obtained from *Echis carinatus* venom on adhesion of Jurkat cells to immobilized VCAM-1 (FIG. 2A) and K562 cells to immobilized fibronectin (FIG. 2B).
Figure 2B:
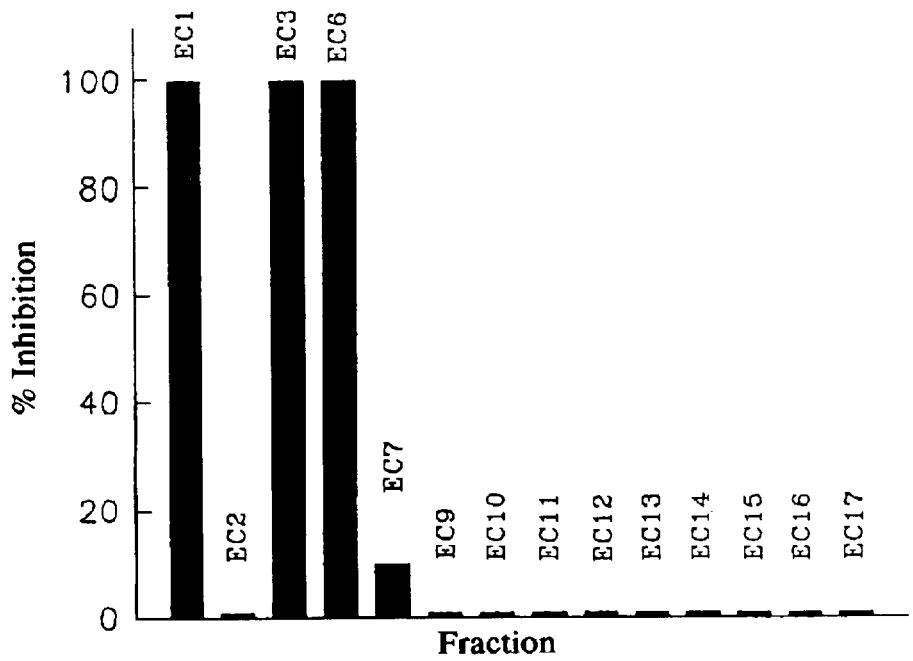

The cell adhesion assay (as described in Example 1) was used to study the inhibitory effect of the eluted fractions on Jurkat cell adhesion to immobilized VCAM-1 and on K562 cell adhesion to fibronectin. Recombinant VCAM-1 (0.5

μg/well) or fibronectin (0.5 μg/well) were immobilized overnight at 4° C. on a 96-well plate (Falcon) in PBS buffer. After blocking, the CMFDA-labeled cells were added to each well in the presence of 5 μg per sample of protein from selected fractions. The results are shown in FIG. 2.

Two fractions, EC3 and EC6, showed significant inhibitory effects on Jurkat cell binding to immobilized VCAM-1. Three fractions: EC1 (echistatin), EC3, and EC6 inhibited binding of K562 cells to immobilized fibronectin. EC3, which eluted at approximately 40% acetonitrile, migrated on SDS-PAGE with an apparent Mr=14 kDa under non reducing conditions and about 7 kDa under reducing conditions, and was relatively free of contaminants.

Example 3

Purification of EC-3

The venom fraction eluting at approx. 40% and designated EC3 was purified to homogeneity by two steps of reverse phase HPLC using a C-18 column. In the first step, proteins from crude venom were separated as in Example 2. The column was eluted with an acetonitrile linear gradient 0–80% over 45 minutes, and the EC3 fraction eluting at approximately 40% of acetonitrile was collected, lyophilized, and dissolved in water. The recovery of protein after the first step was 7 mg per 1 g of dried venom. An aliquot of 0.6 mg of protein isolated in the first step was re-injected into the same HPLC column and eluted with a "flatter" 0–60% acetonitrile gradient over 45 min. The main peak containing EC-3 was collected and lyophilized. The yield of purified EC-3 after the second step was 4 mg per 1 g of crude venom. The purity of EC-3 was tested by SDS-PAGE and mass spectrometry. The molecular mass of EC-3, as determined by electrospray ionization mass spectrometry, was 14,762±1.4 Da. After reduction, major molecular ions at 7369 Da and 7412 Da were observed.

Example 4

Characterization of EC-3

A. Subunit Structure

The reduction and alkylation of EC-3 were performed according to a procedure used for trigramin (Huang et al., *J. Biol. Chem.* 262:16157–63 (1987)). Briefly, 100 μg of EC-3 was incubated in 200 μl of 6 M guanidine hydrochloride, 4 mM EDTA, 0.1 M Tris-HCl, pH 8.5, 3.2 mM dithiothreitol, and 2 μl of vinyl pyridine. The reaction mixture was incubated for two hours at room temperature in the dark, then applied to a C-18 HPLC column and eluted with an acetonitrile gradient (0–80% over 45 min.). In some experiments EC-3 subunits were reduced and carboxymethylated with iodoacetate acid followed by HPLC separation.

Figure 3:
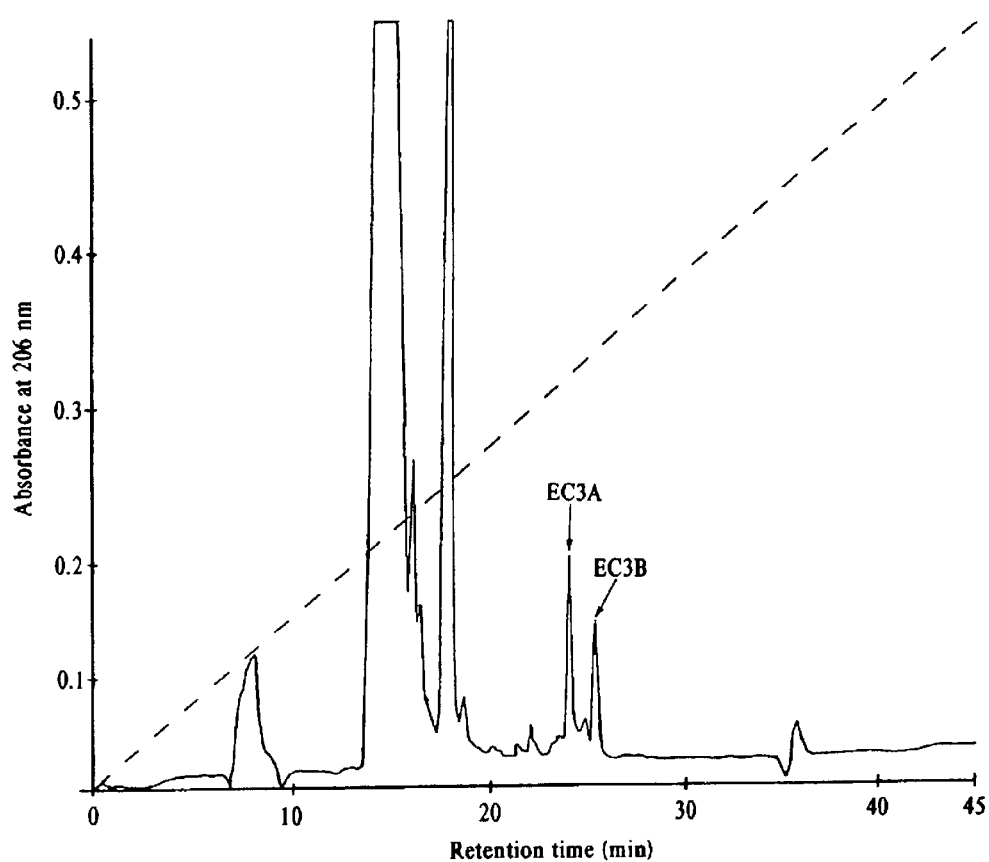
FIG. 3 shows the elution profile of reduced and alkylated EC-3 from a reverse phase HPLC column eluted with an acetonitrile gradient (dashed line). Fractions containing EC3A and EC3B are indicated.

As shown in FIG. 3, after reduction and alkylation with vinylpyridine EC-3 separated into two subunits EC3A and EC3B (epEC3A and epEC3B) which eluted at about 42% and 46% acetonitrile respectively. Electrospray ionization mass spectrometry of epEC3A yielded a major ion at 8478±2 Da. The major molecular ion in carboxymethylated EC3B samples had mass 7950±1 Da.

B. Amino Acid Sequence

The N-terminal sequence of native EC3 electroblotted onto PVDF membrane (Madsudaira, *J. Biol. Chem.* 262:10035–10038 (1987)) and residues 1–40 of epEC3A and epEC3B were determined by N-terminal sequence analysis using an Applied Biosystem Precise instrument. The primary structures of EC3A and EC3B were deduced from Edman degradation of overlapping peptides obtained by digestion with endoproteinaso Lys-C (Boehringer Mainhem) (2 mg/ml protein in 100 mM ammonium bicarbonate, pH 8.3, for 18 h at 37° C. using an enzyme: substrate ratio of 1:100 (w/w)) and CNBr (10 mg/ml protein and 100 mg/ml CNBr in 70% formic acid for 6 h under $N_2$ atmosphere and in the dark). Peptides were separated by reverse-phase of HPLC using a 0.4×25 cm LICHROSHPER RP100C-18 (5 μm particle size) column Merck) eluted at 1 ml/min with acetonitrile gradient. For determination of sulfhydryl groups (free cysteines), native EC3 (2 mg/ml in 100 mM ammonium bicarbonate, pH 8.3 containing 6 M guanidine hydrochloride) was treated for 2 h at room temperature with 100-fold molar excess of iodoacetamide, dialyzed against distilled water, lyophilized and subjected to amino acid analysis (after sample hydrolysis with 6 N HCl for 18 h at 110° C.) using a Pharmacia AlphaPlus amino acid analyzer.

Figure 4A:
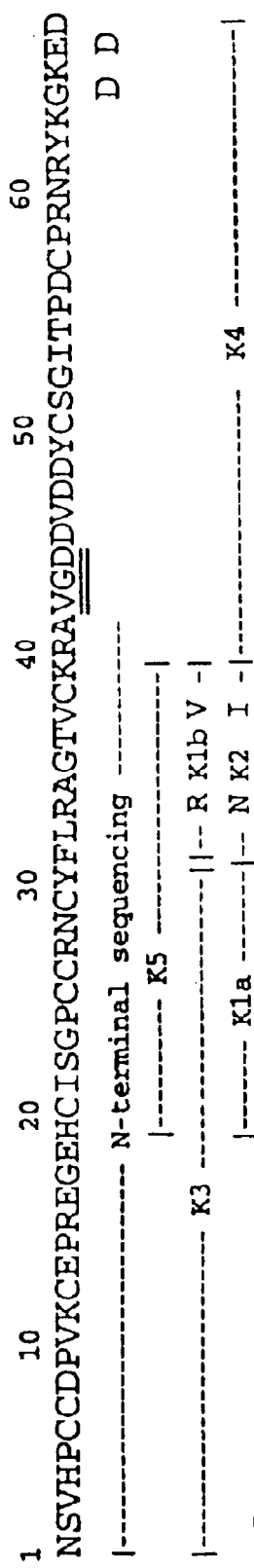
FIG. 4A) and EC-3B (SEQ ID Nos:20 and 3.
Figure 4B:
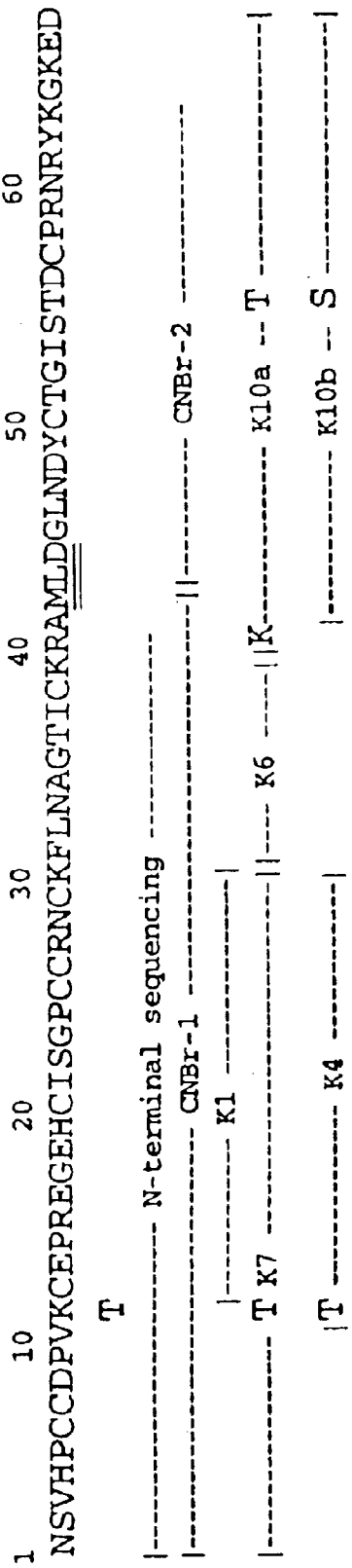
FIG. 4B), which were established by N-terminal sequencing of reduced and ethylpyridylethylated subunits and by sequencing of peptides isolated from digests with endoproteinase Lys-C. EC-3B was also digested by CNBr and two peptides were isolated.

Analysis of the non reduced EC-3 band excised from the Immobilon-P revealed a single amino acid sequence: NSVHPXXDPV(K/T)XEPREGEHXISGP(SEQ ID NO:1). The complete amino acid sequence of EC3A and EC3B, which is shown in FIG. 4, was determined by N-terminal sequence analysis of reverse phase HPLC-isolated peptides derived from degradation of each subunit with endoproteinase Lys-C and CNBr.

Both, EC3A and EC3B are cysteine-rich proteins of 67 amino acids and display heterogeneity at several positions, indicating the existence of isomorphs (isomorphs are given as SEQ ID NOs:19 and 20; the predicted major isomorphs are given as SEQ ID NOs:2 and 3). The isotope-averaged molecular masses calculated for the reduced EC3A isomorphs (1–67: N33 I37 G64 E66), (1–67: R33, V37, G64, E66), and (1–66: N33, I37, D64, D66) are 7412 Da, 7440, Da and 7341 Da, corresponding to major and minor ions of reduced EC-3 mass spectrum. The major EC3A isomorph might be that with molecular weight 7412, which yields a mass of 8476 after reduction and ethylpyridylation. On the other hand, reduced EC3B isomorphs (1–67: T11, K40, S55), (1–67: K11, R40, T55), and (1–67: T11, R40, T55) have calculated masses, 7370 Da, 7439 Da, and 7412 Da, respectively. The major EC3B isomorph, i.e. the one that would have a molecular mass of 7950 after reduction and carboxymethylation, is EC3B 7370 Da. The various EC3A and EC3B isomorphs could combine into a number of dimers. EC3A–EC3B heterodimers may represent the major species, however, because i) homodimers would not yield separated subunits displaying the distinct biological activities demonstrated for HPLC purified A and B fractions, and ii) a mixture of EC3A and EC3B homodimers would display a more complex HPLC separation profile.

As illustrated in FIG. 5, EC3A and EC3B show a high degree of sequence similarity between themselves and with eristostatin (Gould et al., *Proc. Soc. Exp. Biol. Med.* 195:168–71 (1990)), echistatin (Gan et al., *J. Biol. Chem.* 263:19827–32 (1988)), flavoridin (Musial et al, *Circulation* 82:261–73 (1990)), and kistrin (Dennis et al., *Proc. Natl. Acad. Sci. U.S.A.* 87: 2471–75 (1990)), including alignment of conserved cysteines identified in each subunit. The EC3A amino acid sequence has high homology with the disintegrin domain of Le3, a metalloproteinase-disintegrin identified in *Vipera lebetina* (Siigur et al., *Biochem. Biophys. Res. Commun.* 224: 229–236 (1996)). Surprisingly, neither EC3 subunit contains an RGD or KGD sequence. This motif is substituted by VGD in EC-3A and by MLD in EC-3B. The hairpin loops in disintegrins described to date are maintained in appropriate conformation by S-S bridges, and the same appears to be true of EC-3. The hair pin loop sequence of echistatin KRARGDDMDDY (SEQ ID NO:4) is substituted in EC3A and EC3B with KRAVGDDVDDY (SEQ ID NO:5) and KRAMLDGLNDY (SEQ ID NO:6), respectively. It is likely that the integrin binding sites of EC-3 are located in the two loops encompassing Cys38 to Cys50.

Example 5

Biological Activities of EC-3

A. Effect of EC-3 on Jurkat Cell Adhesion to Immobilized VCAM-1

The following experiment demonstrated that EC-3 inhibits the adhesion of Jurkat cells to VCAM-1.

Figure 6:
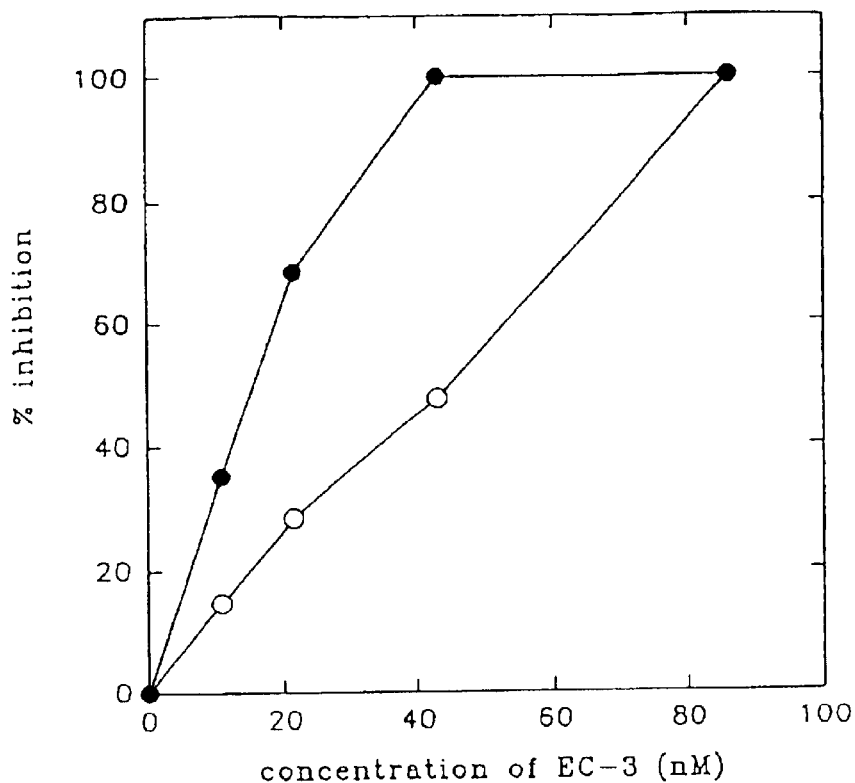
FIG. 6 shows the effect of EC-3 on Jurkat cell adhesion to immobilized VCAM-1 in the presence (filled circles) or absence (open circles) of 1 mM $Mn^{++}$.

Recombinant human VCAM-1 (0.5 µg/well) was immobilized in the wells of an ELISA plate overnight in PBS buffer. The plate was blocked using HBSS buffer containing 1% BSA. CMFDA-labeled Jurkat cells ($1 \times 10^{53}$ cells per sample) were added to the wells in the presence or absence of EC-3 in HBSS buffer containing 1% BSA. The plate was incubated for 30 minutes at 37° C. Unbound cells were removed by aspiration and the wells were washed with HBSS buffer. The bound cells were lysed with 0.5% TRITON® X-100 (alpha-[4-(1,1,3,3-tetramethylbutyl)phenyl]-omega-hydroxypoly(oxy-1,2-ethanediyl), and fluorescence was measured. Percent inhibition was calculated by comparing the fluorescence obtained for adhered cells in the absence (0% inhibition) and presence of EC-3. FIG. 6 shows the percent inhibition with increasing concentrations of EC-3, in the presence (filled circles) or absence (open circles) of 1 mM $Mn^{++}$.

B. Effect of EC-3 on α4B2 Cell Adhesion to Immobilized VCAM-1

The following experiment demonstrated that EC-3 inhibits the adhesion of Chinese hamster ovary cells, which are α5 deficient (B2 cells) and have been transfected with human α4 integrin, to VCAM-1.

Figure 7:
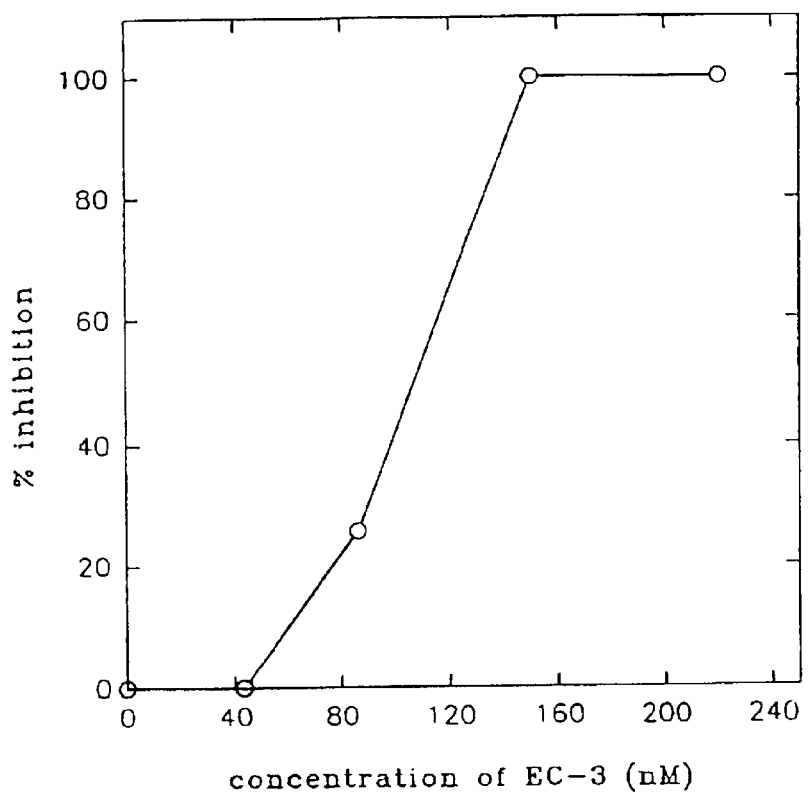
FIG. 7 shows the effect of EC-3 on CHO (α4+, α5−) cell adhesion to immobilized VCAM-1.

Chinese hamster ovary cells transfected with human α4 integrin were provided by Dr. Y. Takada (Scripps Research Institute, La Jolla, Calif.). Recombinant human VCAM-1 (0.5 µg/well) was immobilized in the wells of an ELISA plate overnight in PBS buffer. The plate was blocked using HBSS buffer containing 1% BSA. CMFDA-labelled α4B2 cells ($1 \times 10^5$ cells per sample) were added to the wells in the presence or absence of EC-3 in HBSS buffer containing 1% BSA. The plate was incubated for 1 hour at 37° C. Unbound cells were removed by aspiration and the wells were washed with HBSS buffer. The bound cells were lysed with 0.5% Triton X-100, and fluorescence was measured. FIG. 7 shows the percent inhibition with increasing concentrations of EC-3.

C. Comparison of the Anti-Adhesive Effects of EC-3 and Echistatin

Figure 8:
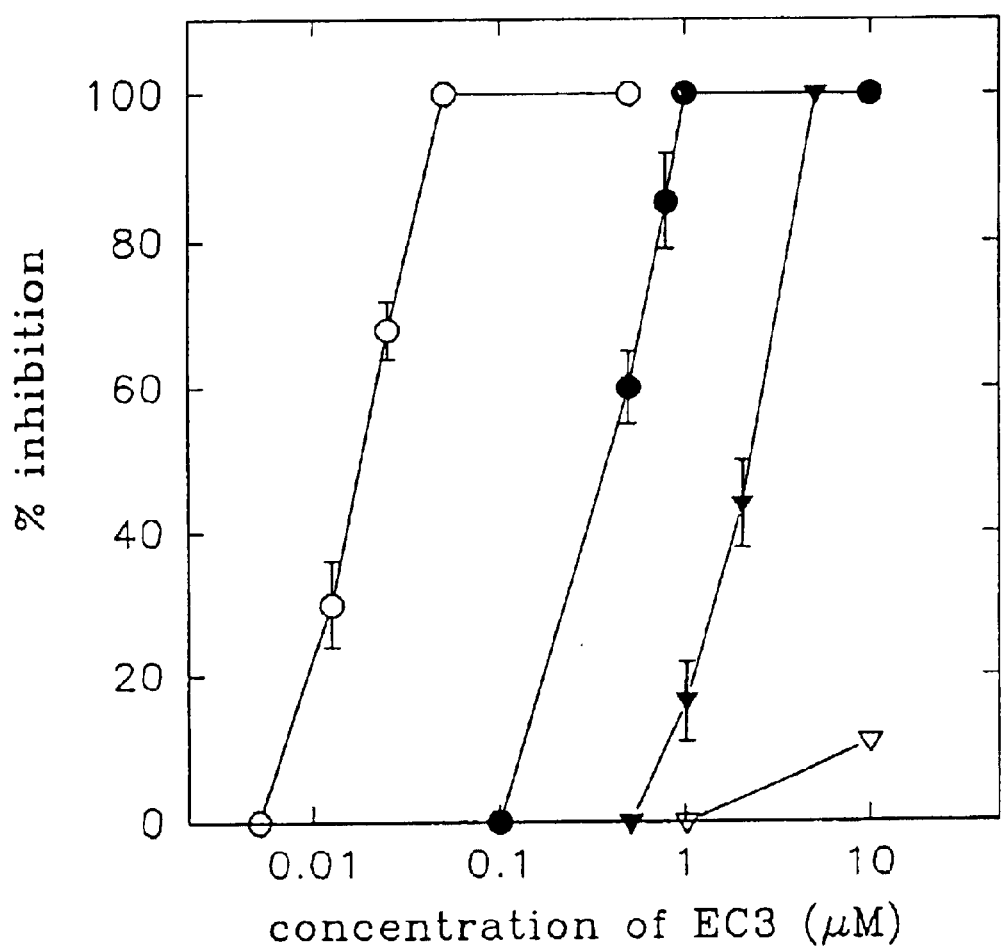
FIG. 8 shows the effect of EC3 on the adhesion of CHO cells transfected with different integrins. Adhesion experiments were performed using Chinese hamster ovary (CHO) cells transfected with different human integrins. Open circles show the effect of EC-3 on the adhesion of CHO cells transfected with α4 to immobilized VCAM-1; closed circles: CHO cells transfected with αIIbβ3 to fibrinogen; open triangles: CHO cells transfected with αvβ3 to vitronectin; and closed triangles: non-transfected CHO cells expressing hamster α5β1 to fibronectin. Error bars represent S.D. from three experiments.

The biological activities of EC3 and the RGD-containing disintegrin echistatin were compared in a panel of integrin assays, the results of which are shown in FIGS. 6–8 and Table 1.

The effect of each peptide on cell adhesion was determined as described above. Briefly, ligands were immobilized or ELISA plates then incubated with cells labeled with CMFDA in the presence of various concentrations of EC-3 or echistatin. Cells that attached to the plates were lysed with detergent, and fluorescence intensity was measured. Percent inhibition was measured at each concentration and $IC_{50}$ was determined.

First, RGD-selective integrins were evaluated. As expected, echistatin at concentrations of 20–130 nM potently inhibited αIIbβ3-dependent platelet aggregation and αIIbβ3-, αvβ3-, and α5β1-dependent cell adhesion (Table 1). In contrast, EC3 only weakly inhibited αIIbβ3-dependent interaction ($IC_{50}$ 1 AM for platelet aggregation and 500 nM for A5 cell adhesion to fibrinogen, respectively) and showed no inhibition of αvβ3-dependent adhesion up to 10 µM, although inhibition of α5β1-dependent adhesion was observed at 150 nM $IC_{50}$.

TABLE 1

Comparison of the Inhibitory Effects of Echistatin and EC3 on Various Integrins.

| | | | | $IC_{50}$, nM | |
| Cell suspension | Integrin | Ligand | Assay | Echistatin | EC3 |
| --- | --- | --- | --- | --- | --- |
| Platelets | αIIbβ3 | Fg | ADP PA | 130 | 1000 |
| A5 (CHOαIIbβ3+) | αIIbβ3 | Fg | CA | 50 | 500 |
| VNRC3 (CHOαvβ3+) | αvβ3 | Vn | CA | 50 | >$10^4$ |
| K562 | α5β1 | Fn | CA | 20 | 150 |
| K562 (α6+) | α6β1 | Lm | CA | >$10^4$ | >$10^4$ |
| A2 (CHOα4+) | α4β1 | VCAM-1 | CA | >$10^4$ | 30 |
| α4B2 (CHO-α4+/α5−) | α4β1 | VCAM-1 | CA | >$10^4$ | 30 |
| Jurkat | α4β1 | VCAM-1 | CA | >$10^4$ | 25 |
| Jurkat | α4β1 | VCAM-1 | DBA | ND | 28 |
| Jurkat | α4β1 | CS-1 | CA | ND | 100 |
| JY | α4β7 | VCAM-1 | DBA | ND | 6 |
| RPMI 8866 | α4β7 | MadCAM-1 | CA | >$10^4$ | 5 |

Fg = fibrinogen;
Fn = fibronectin;
Vn = vitronectin;
CS-1 = conective segment 1 of fibronectin;
Lm = laminin;
PA = platelet aggregation;
CA = cell adhesion;
DBA = direct binding assay;
ND = not determined When the two disintegrins were evaluated in a panel of α4 integrin cell adhesion assays the specificities were reversed. At concentration of 20–300 nM EC3 was a highly potent inhibitor of the interaction of both anchorage-dependent and anchorage-independent cells expressing α4β1 with either VCAM-1 or the CS-1 fragment of fibronectin, while echistatin showed no detectable activity at 10 µM. EC3 inhibited to the same extent adhesion of A2 (CHOα4+α5+) cells and α4B2 (CHOα4+α5−) cells to immobilized VCAM-1, confirming direct inhibition of α4β1 integrin. To further extend the data on α4 integrins, the potency of EC3 in assays measuring VCAM-Ig binding directly to either α4β1 on Jurkat cells or α4β7 on JY cells was evaluated. EC3 potently inhibited α4β1 and α4β7 binding at concentrations 28 nM and 6 nM, respectively. These data both confirm the specificity of EC3 for α4 integrins in an assay distinct from cell adhesion, and show its high potency on integrin α4β7.

D. Effect of HP 2/1 Monoclonal Antibody, GRGDSP (SEQ ID NO:12), and GRGESP (SEQ ID NO:13) Peptides and on Jurkat Cell Adhesion to Immobilized EC-3

Further experiments showed that EC3 competes with mab HP2/1, which recognizes the N-terminal domain of α4 integrin. HP 2/1 at a concentration of 1 µg per sample blocked adhesion of Jurkat cells to immobilized EC3, whereas the hexapeptide GRGDSP (SEQ ID NO:12) at a concentration of 1 mM was not effective.

Figure 9A:
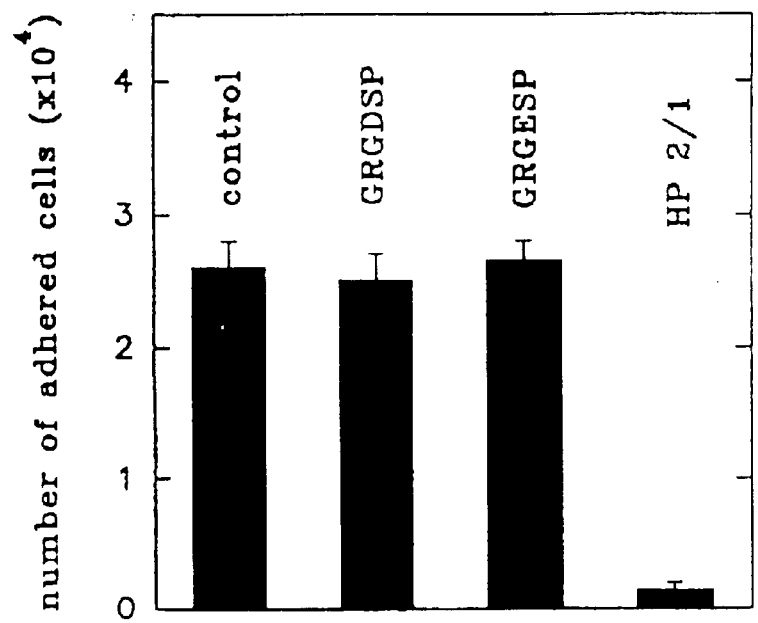
FIG. 9A shows the effect of GRGDSP (SEQ ID NO:12), GRGESP (SEQ ID NO:13) and HP 2/1 monoclonal antibody on the adhesion of Jurkat cells to immobilized EC-3.
Figure 9B:
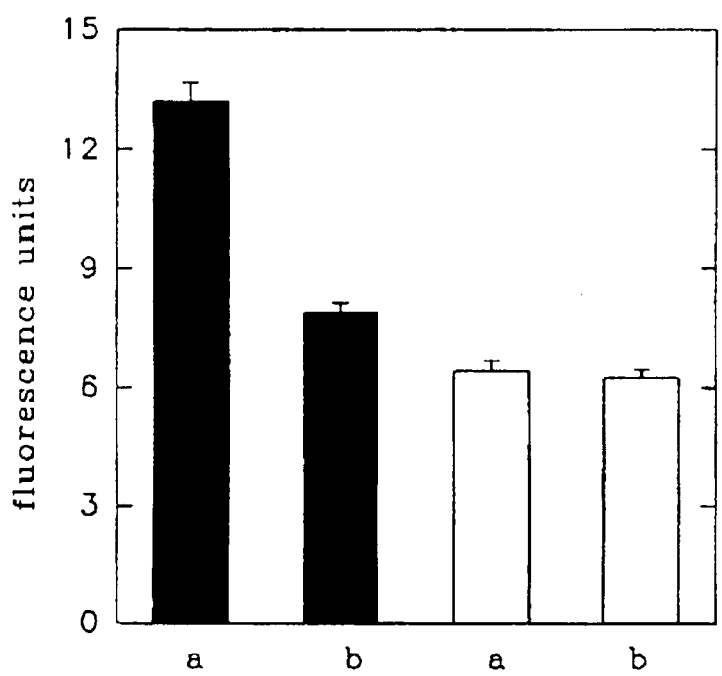
FIG. 9B shows the effect of EC-3 on the binding HP 2/1 monoclonal antibody to cells expressing α4β1 integrin. Error bars represent the S.D. from three experiments.

FIG. 9A shows the effect of GRGDSP (SEQ ID NO:12), GRGESP (SEQ ID NO:13) and HP 2/1 monoclonal antibody on the adhesion of Jurkat cells to immobilized EC3. The adhesion study was performed using CMFDA-labeled Jurkat cells in the absence or presence 1 mM GRGDSP or GRGESP, or 10 µg/ml HP 2/1. Competition between EC3 and HP2/1 was also confirmed in cell suspension using FACS analysis. FIG. 9B shows inhibition of HP2/1 binding to α4B2 cells. The experiment was performed using flow cytometry. Jurkat cells (open bars) or B2-CHO cells (CHO cells with deleted α5 transfected with α4) (closed bars) were incubated with 10 µg/ml HP 2/1 in the absence (a) or presence 60 nM EC3 (b) for 30 min at room temperature. After washing, 10 µg/ml of FITC-conjugated goat anti-mouse IgG was added and samples were incubated for another 30 min at room temperature. The samples were fixed by addition of 1% paraformaldehyde before measurement of fluorescence intensity. No inhibitory effect was observed in Jurkat cells, which express both α5β1 and α4β1.

Figure 10:
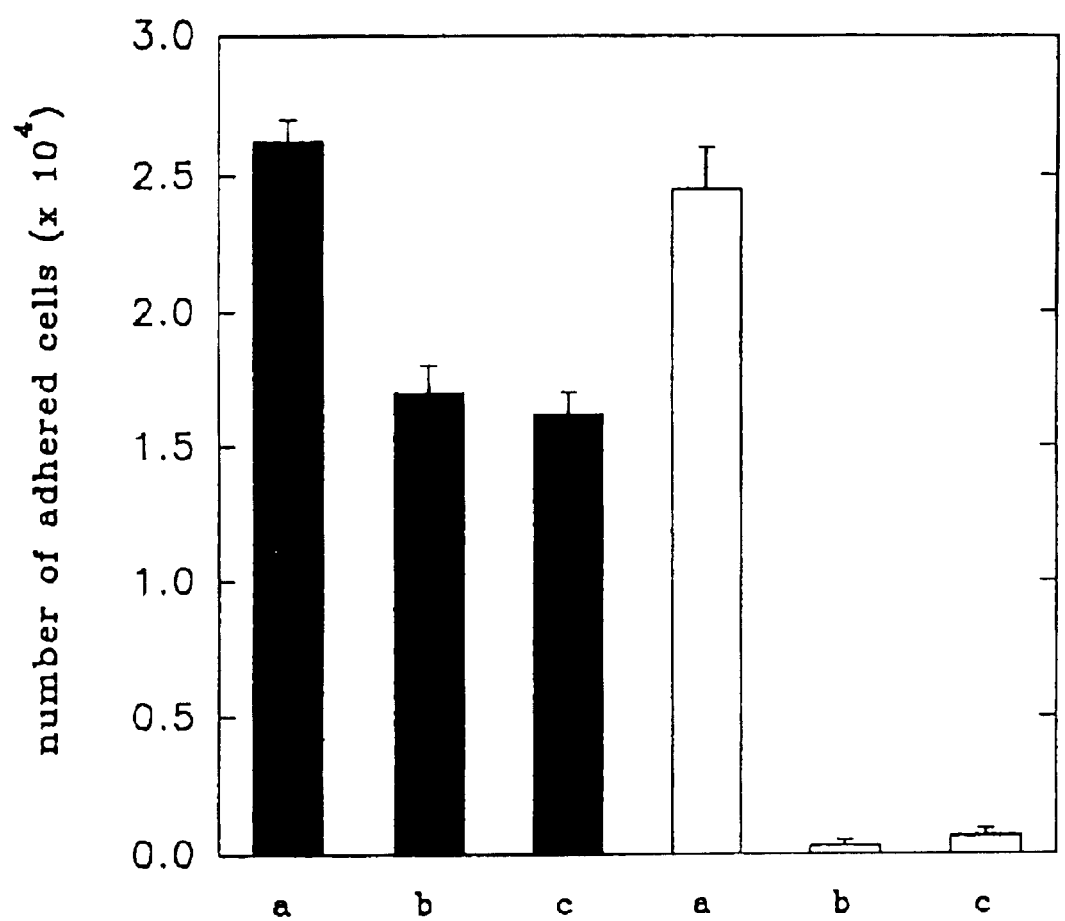
FIG. 10 shows the adhesion of CHO cells transfected with α4 and with α4 inactive G190A mutant to immobilized EC-3 and to immobilized HP2/1 antibody. The number of adhered cells is shown for: (a) CHO cells transfected with wild-type α4, (b) CHO cells transfected with G190A α4, (c) control CHO-K1 cells. The results with EC-3 are shown as open bars, and the results with HP2/1 are shown as closed bars. Error bars represent S.D. from three experiments.

FIG. 10 shows the adhesion of CHO cells transfected with α4 and with α4 inactive G190A mutant to immobilized EC3 and to immobilized HP2/1 antibody. EC3 (2 µg/well) and HP2/1 (1 µg/well) were immobilized on the 96well plate. The CHO cells were labeled with CMFDA and adhesion was performed as described above. The inactive G190A α4 mutant did not interact with EC3, since adhesion of CHO transfected with this mutant to immobilized EC3 was identical with adhesion of non transfected cells. Only A2 cells expressing wild type α4 adhered to immobilized HP2/1. In addition, the ability to inhibit directly α5µl was confirmed using mab SAM-1, which blocked adhesion of K562 cells to immobilized EC3. Finally, neither echistatin nor EC3 inhibited adhesion to laminin of K562 cells transfected with α6 at concentration 10 µM (see Table 1).

E. Platelet Aggregation Assay

Blood from a healthy donor was collected into a syringe containing sodium citrate as an anticoagulant. The anticoagulated blood was centrifuged at 400 g for 17 minutes, and platelet rich plasma (PRP) was removed by aspiration. The aggregation of platelets in PRP in the presence of 30 µM ADP was measured in the absence and presence of echistatin and EC-3, using an aggregation meter (Sinco).

Echistatin and EC-3 inhibited ADP induced platelet aggregation with an $IC_{50}$ of 130 nM and 1,000 nM, respectively.

Example 6

Biological Activity of EC-3 Peptides

A. Biological Activity of the EC-3 Subunits

Figure 11A:
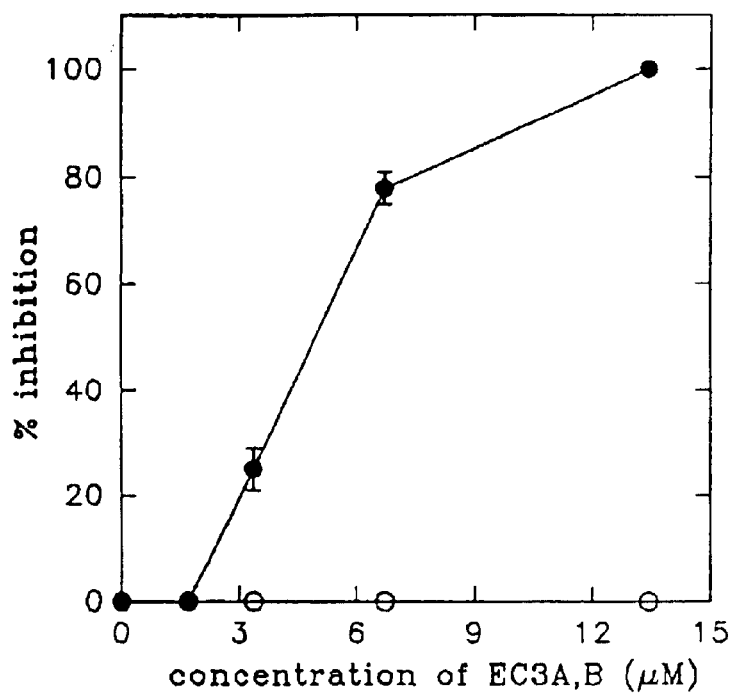
FIG. 11 shows the effect of reduced and ethylpyridylethylated EC3A (open circles) and EC3B (closed circles) on adhesion of Jurkat cells to immobilized VCAM-1 (FIG. 11A) and K562 cells to immobilized fibronectin (FIG. 11B). Error bars indicate S.D. from three experiments.
Figure 11B:
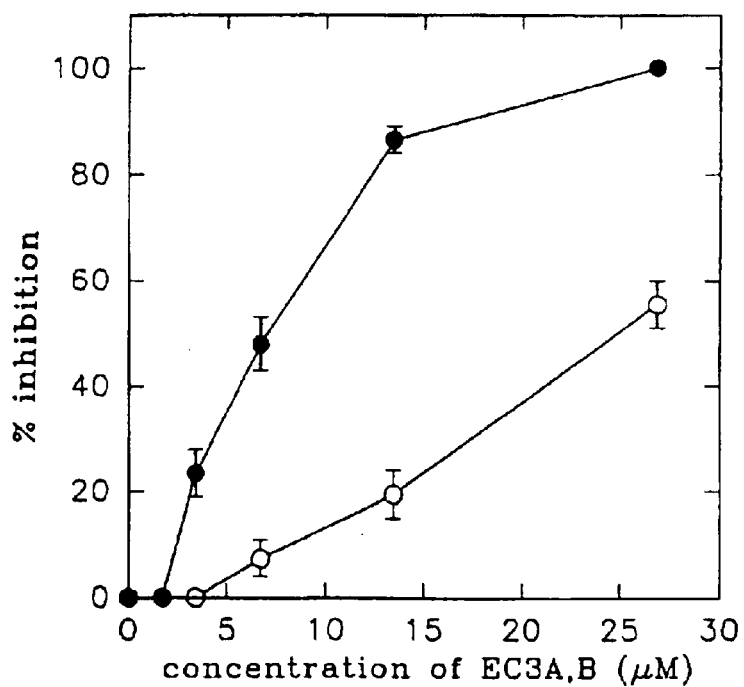

The biological activity of EC-3A and EC-3B subunits after reduction and ethylpyridylethylation was also evaluated. Although activity of both subunits was significant, it was decreased by approximately 200 fold as compared to EC-3. It has been previously reported that reduction and ethylpyridylethylation of flavoridin and albolabrin decreased their ability to inhibit ADP-induced platelet aggregation by 40 fold approximately (Calvete et al., *Biochemistry* 30, 5225–5229 (1991)). As shown in FIG. 11, epEC3B inhibited adhesion of Jurkat cells to immobilized VCAM-1 with $IC_{50}$=6 µM whereas epEC3A was inactive in this system. However, epEC3A and epEC3B both inhibited adhesion of K562 cells to fibronectin with $IC_{50}$=30 µM and 6 µM, respectively. This experiment suggests that the specificity of EC-3 for α4 integrins likely resides in the MLD sequence in EC-3B subunit, whereas the ability of EC-3 to inhibit α5β1 likely resides in both subunits.

B. Biological Activity of EC-3 Synthetic Peptides

The RGD motif in monomeric disintegrins is replaced by MLDG (SEQ ID NO:14) in EC-3B. Both RGD and MLDG may therefore represent integrin binding sites.

Figure 12:
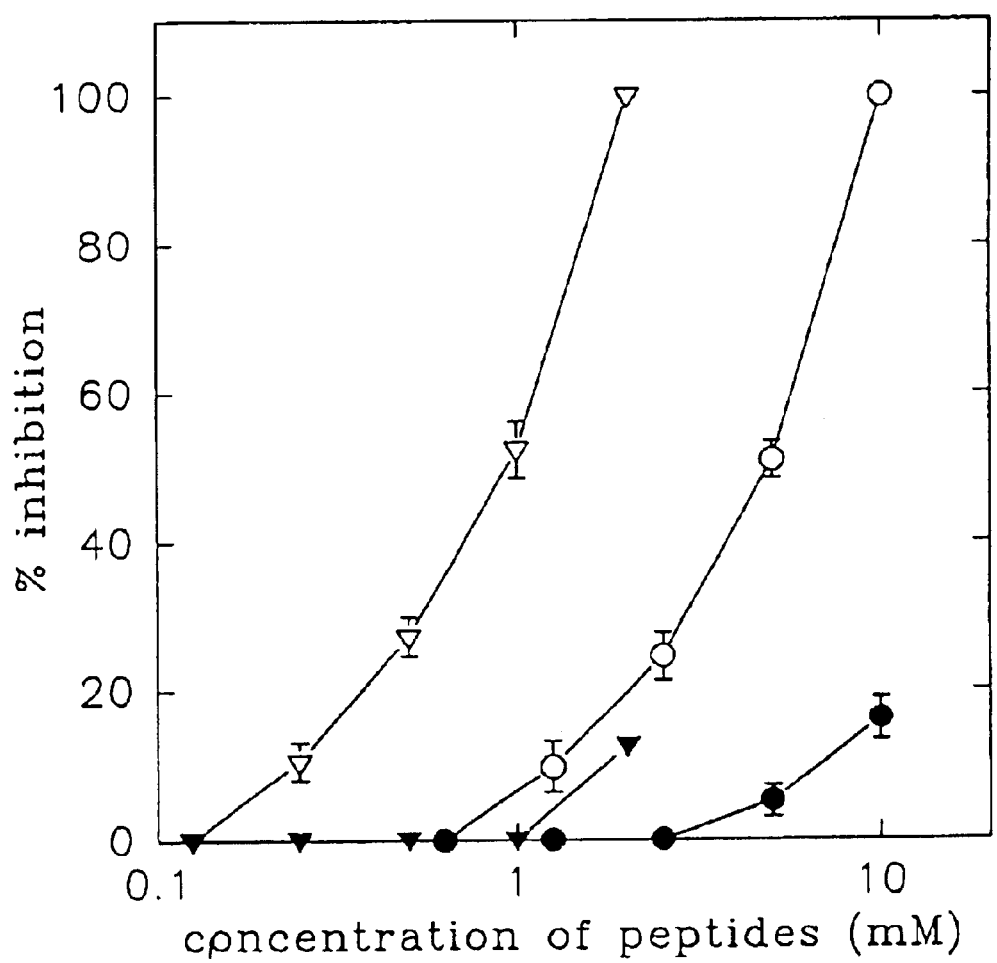
FIG. 12 shows the effect of EC-3B derived peptides on Jurkat cell adhesion to immobilized VCAM-1. The inhibitory effect of MLDG peptide (SEQ ID NO:14) is shown by open circles, RGDS peptide (SEQ ID NO:15) by closed circles, cyclic *CKRAMLDGLNDYC* (SEQ ID NO:16) by open triangles and *CKRAMLAGLNDYC* (SEQ ID NO:17) by closed triangles. Error bars indicate S.D. from three experiments.

A linear MLDG (SEQ ID NO:14) synthetic peptide was synthesized using solid phase methodology. As shown in FIG. 12, the linear MLDG peptide (SEQ ID NO:14) inhibited adhesion of Jurkat cells to immobilized VCAM-1 with $IC_{50}$=5 mM. An RGDS peptide (SEQ ID NO:15), which is a known inhibitor of several β1 and β3 integrins, was inactive at this concentration.

Two 13-amino acid peptides cyclized through Cys—Cys residues were synthesized on an automated peptide synthesizer by assembly on 4-benzyloxybenzyl alcohol resin. Piperidine/toluene were used for removal of the $N^{α}$-9-fluorenylmethyl-oxycarbonyl (Fmoc) group. Neutralization and coupling were carried out in N-methylpyrrolidinone. The benzotriazole-N, N, N', N'-tetramethyl-uronium hexafluorophosphate (HBTU)/1-hydroxybenzotriazole-mediated coupling efficiency was determined by a quantitative ninhydrin analysis. Removal of the side-chain protecting groups and cleavage of the assembled peptide from the resin were achieved by treating with trifluoroacetic acid in the presence of ethane dithiol, crystalline phenol, thioanisole and tri-isopropyl silane as scavengers. The peptides were purified using HPLC on C18 column with a water/acetonitrile gradient, containing 0.1% TFA. The amino acid composition of the peptides was determined by the Pico Tag method, and the molecular mass of the peptides was confirmed using Mass spectrometry.

The cyclic peptide CKRAMLDGLNDYC (Cys Lys Arg Ala Met Leu Asp Gly Leu Asn Asp Tyr Cys, SEQ ID NO:16), representing a putative hair pin loop of EC3B was five fold more active ($IC_{50}$=1 mM) than MLDG (SEQ ID NO:14) in molar ratio. The cyclic peptide CKRAMLA$^7$GLNDYC (SEQ ID NO:17), in which $D^7$ was substituted with alanine, had no significant activity in inhibition of Jurkat cells/VCAM-1 interaction.

Additional peptides, comprising fragments and derivatives of EC-3 such as Met Leu Asp Gly Leu (SEQ ID NO:18), are synthesized and inhibitory activity is measured using assays such as those described in Example 5.

C. Biological Activity of Modified Echistatin Peptides

Using standard methods of recombinant DNA technology, a modified echistatin polypeptide is produced. In the modified echistatin, the Arg-Gly-Asp residues at positions 24–26 are replaced by Met-Leu-Asp. The biological activity of the modified echistatin, as well as fragments and derivatives thereof, is determined.

Example 7

Effect of EC-3 on Lymphocyte Infiltration of Langerhans Islets in Non Obese Diabetic (NOD) Mice A. The NOD Mouse Model Lymphocyte extravasation is essential to the normal immune response. Lymphocyte reticulation and accumulation at a site of inflammation is a multistep process which involves interaction between lymphocyte adhesion molecules and their endothelial ligands.

Non Obese Diabetic (NOD) mice develop an age related lymphocyte infiltration of pancreatic islets and salivary glands, which resembles human type I diabetes and Sjogren's syndrome. Studies on the adhesion molecules involved in lymphocyte invasion of pancreas and salivary glands in NOD mice have suggested that the integrins α4β1 and α4β7 are important for infiltration of Langerhans islets in the pancreas.

The following experiment showed that EC-3, which selectively inhibits α4 integrins, can block lymphocyte invasion of pancreatic parenchyma in NOD mice. Echistatin, which inhibits αvβ3- and α5β1-dependent interactions, but not α4-dependent interactions, was inactive in this experiment.

B. Treatment of Mice

Female NOD mice from 1 to 5 weeks of age were purchased from Jackson Laboratory (Bar Harbor, Me.).

The mice were divided into 3 groups, and each group was treated with PBS, echistatin, or EC-3 for nine weeks. The PBS, echistatin, and EC-3 were administered intraperitoneally in a total volume of 0.5 ml three times per week. The treatment groups were: (a) PBS (control); (b) 1 µg/mouse of echistatin; and (c) 3 µg/mouse of EC-3. The 3 µg/mouse EC-3 dose is the molar equivalent of the 1 µg/mouse echistatin dose, since the molecular weight of EC-3 is approximately three times that of echistatin.

After nine weeks of treatment the animals were sacrificed by exposure to $CO_2$. The pancreas was removed, frozen, and stored at −70° C. until the histological analysis. For the histological analysis, five µm sections of frozen tissue were fixed with acetone. For detection of infiltrating lymphocytes, the sections were stained with hematoxylin/eosin, and observed by light microscopy.

C. Results

The results are shown in Table 2. Treatment with EC-3 reduced the level of lymphocyte infiltration in pancreatic islets of NOD mice, while treatment with echistatin was ineffective.

TABLE 2

Effect of EC-3 and Echistatin on the Infiltration of Pancreatic Langerhans Islets in NOD Mice

| Group | Number of Animals | | Number of Islets | | | | |
| | Total | without infiltration | Total | Infiltration Score | | | |
| | | | | − | + | ++ | +++ |
| PBS | 8 | 0 | 25 | 1 | 5 | 10 | 9 |
| Echistatin | 10 | 0 | 27 | 5 | 2 | 10 | 10 |
| EC-3 | 10 | 2 | 29 | 10 | 12 | 7 | 0 | infiltration score:
−: no infiltration
+: periinsular infiltration
++: ⅓ of the islet infiltrated
+++: ½ or more of the islet infiltrated All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

We claim:

1. A substantially purified EC3 protein isolated from *Echis carinatus* venom, characterized by:
   (a) an apparent molecular mass of about 14,762 Da, as determined by electrospray ionization mass spectrometry;
   (b) elution from a C-18 high performance liquid chromatography column at about 40% acetonitrile; and
   (c) the ability to inhibit adhesion of Jurkat cells to vascular cell adhesion molecule-1.

2. A substantially purified EC-3A peptide isolated from EC-3 protein which has been reduced and alkylated, characterized by:
   (a) a molecular mass of about 8478 Da in its ethylpyridylated form, as determined by electrospray ionization mass spectrometry;
   (b) elation from a C-18 high performance liquid chromatography column at about 42% acetonitrile; and
   (c) the ability to inhibit adhesion of K562 cells to fibronectin.

3. A substantially purified EC-3B peptide isolated from EC-3 protein which has been reduced and alkylated with vinylpyridine, characterized by:
   (a) a molecular mass of about 7950 Da in its carboxymethylated form, as determined by electrospray ionization mass spectrometry;
   (b) elution from a C-18 high performance liquid chromatography column at about 46% acetonitrile; and
   (c) the ability to inhibit adhesion of Jurkat cells to vascular cell adhesion molecule-1.

4. The substantially purified EC-3A peptide of claim 2 comprising a sequence represented by SEQ ID NO:19 or a fragment characterized by the ability to inhibit adhesion of K562 cells to fibronectin thereof.

5. The substantially purified EC-3A peptide of claim 2 comprising a sequence represented by SEQ ID NO:2.

6. The substantially purified EC-3B peptide of claim 3 comprising a sequence represented by SEQ ID NO:20, or a fragment characterized by the ability to inhibit adhesion of Jurkat cells to vascular cell adhesion molecule-1 thereof.

7. The substantially purified EC-3B peptide of claim 3 comprising a sequence represented by SEQ ID NO:3.

8. The substantially purified EC-3 protein of claim 1 comprising two subunits, wherein one subunit comprises the sequence SEQ ID NO:19 or a fragment characterized by the ability to inhibit adhesion of K562 cells to fibronectin thereof and one subunit comprises the sequence SEQ ID NO:20 or a fragment characterized by the ability to inhibit adhesion of Jurkat cells to vascular cell adhesion molecule-1 thereof.

9. The substantially purified EC-3B peptide of claim 6, wherein the biologically active fragment comprises a peptide represented by an amino acid sequence X-Y-Met-Leu-Asp-Z, where X is H or a blocking group, Y is zero or more amino acids, and Z is OH or zero or more amino acids.

10. The substantially purified EC-3B peptide of claim 9, wherein the biologically active fragment comprises a peptide having from about 3 to about 20 amino acids.

11. The substantially purified EC-3B peptide of claim 9, wherein the biologically active fragment is represented by SEQ ID No: 16.

12. The substantially purified EC-3B peptide of claim 9, wherein the biologically active fragment is represented by SEQ ID No. 14.

13. A substantially purified echistatin polypeptide represented by SEQ ID NO: 9, in which the Arg-Gly-Asp residues at positions 24–26 are replaced by M et-Leu-Asp.

14. A method of isolating a peptide from a venom, wherein the peptide binds to an integrin of interest, comprising:
    (a) dissolving venom in a solvent,
    (b) centrifuging the dissolved venom to remove high molecular weight proteins, (c) fractionating the supernatant from step (b), (d) immobilizing the fractions from step (c) on a solid support, (e) adding detectably labeled cells that express the integrin of interest to the immobilized fractions, (f) detecting the number of cells bound to each immobilized fraction, and (g) isolating peptide from those fractions which showed enhanced cell binding in step(f).

15. A composition comprising a pharmaceutically acceptable carrier and the protein or peptide of any of claims 1–12, or a pharmaceutically acceptable salt thereof.

16. A method of inhibiting the binding of an α4 integrin to VCAM-1 comprising contacting a cell that expresses the α4 integrin with an effective amount of a protein or peptide according to one of claims 1–12, or a pharmaceutically acceptable salt thereof.

17. The method of claim 16 wherein the integrin is α4β1 or α4β7.

18. A method of inhibiting the binding of an α4β7 integrin to MadCAM-1 comprising contacting a cell that expresses α4β7 with an effective amount of a protein or peptide according to one of claims 1–12, or a pharmaceutically acceptable salt thereof.

19. A method of inhibiting the binding of an α4 integrin to CS-1 comprising contacting a cell that expresses the α4 integrin with an effective amount of a protein or peptide according to one of claims 1-12, or a pharmaceutically acceptable salt thereof.

20. A method of inhibiting the interaction between cells expressing an α4 integrin and VCAM-1 in a patient in need of such treatment comprising administration of a therapeutically effective amount of a composition according to claim 15.

21. A method of inhibiting the interaction between cells expressing an α4 integrin and MadCAM-1 in a patient in need of such treatment comprising administration of a therapeutically effective amount of a composition according to claim 15.

22. A method of inhibiting the interaction between cells expressing an α4 integrin and CS-1 in a patient in need of such treatment comprising administration of a therapeutically effective amount of a composition according to claim 15.

23. A substantially purified EC-3A peptide characterized by:

(a) a sequence having greater than 90% sequence identity with SEQ ID NO:2; and (b) the ability to inhibit adhesion of K562 cells to fibronectin.

24. A substantially purified EC-3B peptide characterized by:

(a) a sequence having greater than 90% sequence identity with SEQ ID NO:3; and (b) the ability to inhibit adhesion of Jurkat cells to VCAM-1.

* * * * *

UNITED STATES PATENT AND TRADEMARK OFFICE
CERTIFICATE OF CORRECTION

| | | |
|---|---|---|
| PATENT NO. | : 6,818,617 B1 | Page 1 of 1 |
| APPLICATION NO. | : 09/485323 | |
| DATED | : November 16, 2004 | |
| INVENTOR(S) | : Stefan Niewiarowski and Cezary Marcinkiewicz | |

It is certified that error appears in the above-identified patent and that said Letters Patent is hereby corrected as shown below:

Column 1, lines 13-16, cancel the text and insert the following:

--This invention was made with government support under grants HL45486 and HL 19055 awarded by the National Institutes of Health. The government has certain rights in the invention.--

Signed and Sealed this

Fourth Day of October, 2011

David J. Kappos
*Director of the United States Patent and Trademark Office*